(12) United States Patent
Heaton et al.

(10) Patent No.: US 7,488,494 B2
(45) Date of Patent: Feb. 10, 2009

(54) COMPOSITIONS AND THERAPEUTIC METHODS INVOLVING ISOFLAVONES AND ANALOGUES THEREOF

(75) Inventors: Andrew Heaton, Abbotsford (AU); Naresh Kumar, Maroubra (AU); Graham Edmund Kelly, Northbridge (AU); Alan Husband, McMahon's Point (AU)

(73) Assignee: Novogen Research Pty Ltd., North Ryde (AU)

(*) Notice: Subject to any disclaimer, the term of this patent is extended or adjusted under 35 U.S.C. 154(b) by 285 days.

(21) Appl. No.: 10/704,385

(22) Filed: Nov. 7, 2003

(65) Prior Publication Data

US 2004/0147551 A1 Jul. 29, 2004

Related U.S. Application Data

(63) Continuation of application No. 10/070,361, filed as application No. PCT/AU00/01056 on Sep. 6, 2000, now abandoned.

(30) Foreign Application Priority Data

Sep. 6, 1999 (AU) .................. PQ2661

(51) Int. Cl.
- *A61K 47/22* (2006.01)
- *A61K 31/47* (2006.01)
- *C07D 335/04* (2006.01)
- *C07D 311/04* (2006.01)

(52) U.S. Cl. .............. 424/439; 514/312; 514/456; 549/23; 549/406

(58) Field of Classification Search ........... 514/312, 514/456; 546/153; 549/23, 406; 424/439
See application file for complete search history.

(56) References Cited

U.S. PATENT DOCUMENTS

| | | | |
|---|---|---|---|
| 3,471,520 A | 10/1969 | Irmscher et al. |
| 3,535,344 A | 10/1970 | Irmscher et al. |
| 3,973,608 A | 8/1976 | Umezawa et al. |
| 4,157,984 A | 6/1979 | Zilliken |
| 4,200,692 A | 4/1980 | Puls et al. |
| 4,264,509 A | 4/1981 | Zilliken |
| 4,301,251 A | 11/1981 | Rumyantseva et al. |
| 4,366,082 A | 12/1982 | Zilliken |
| 4,390,559 A | 6/1983 | Zilliken |
| 4,428,876 A | 1/1984 | Iwamura |
| 4,814,346 A | 3/1989 | Albert et al. |
| 5,141,746 A | 8/1992 | Fleury et al. |
| 5,153,230 A | 10/1992 | Jaffery |
| 5,247,102 A | 9/1993 | Kállay et al. |
| 5,320,949 A | 6/1994 | Shen |
| 5,352,384 A | 10/1994 | Shen |
| 5,424,331 A | 6/1995 | Shlyankevich |
| 5,498,631 A | 3/1996 | Gorbach et al. |
| 5,506,211 A | 4/1996 | Barnes et al. |
| 5,516,528 A | 5/1996 | Hughes et al. |
| 5,523,087 A | 6/1996 | Shlyankevich |
| 5,530,112 A | 6/1996 | Greenshields et al. |
| 5,547,866 A | 8/1996 | Durzan et al. |
| 5,554,519 A | 9/1996 | Weber et al. |
| 5,569,459 A | 10/1996 | Shlyankevich |
| 5,637,561 A | 6/1997 | Shen et al. |
| 5,639,785 A | 6/1997 | Kung |
| 5,679,806 A | 10/1997 | Zheng et al. |
| 5,700,669 A | 12/1997 | Hanson et al. |
| 5,702,752 A | 12/1997 | Gugger et al. |
| 5,726,034 A | 3/1998 | Bryan et al. |
| 5,733,926 A * | 3/1998 | Gorbach .............. 514/456 |
| 5,763,389 A | 6/1998 | Shen et al. |
| 5,789,581 A | 8/1998 | Matsuura et al. |
| 5,792,503 A | 8/1998 | Gugger et al. |
| 5,804,234 A | 9/1998 | Suh et al. |
| 5,830,887 A | 11/1998 | Kelly |
| 5,855,892 A | 1/1999 | Potter et al. |
| 5,942,539 A | 8/1999 | Hughes, Jr. et al. |
| 6,004,558 A | 12/1999 | Thurn et al. |
| 6,060,070 A | 5/2000 | Gorbach |
| 6,146,668 A | 11/2000 | Kelly et al. |
| 6,235,773 B1 | 5/2001 | Bissett |
| 6,261,565 B1 | 7/2001 | Empie et al. |
| 6,340,703 B1 | 1/2002 | Kelly |
| 6,455,032 B1 | 9/2002 | Kelly et al. |
| 6,497,906 B1 | 12/2002 | Kelly |
| 6,562,380 B1 | 5/2003 | Kelly |
| 6,599,536 B1 | 7/2003 | Kelly et al. |
| 6,642,212 B1 | 11/2003 | Kelly |
| 6,645,951 B1 * | 11/2003 | Jo et al. .............. 514/100 |
| 6,649,648 B1 | 11/2003 | Kelly et al. |
| 2002/0035074 A1 | 3/2002 | Kelly |

FOREIGN PATENT DOCUMENTS

| | | |
|---|---|---|
| AU | B-80655/87 | 5/1988 |
| AU | A-10227/95 | 7/1995 |
| AU | A-24813/97 | 12/1997 |
| AU | A-73072/98 | 9/1999 |
| AU | A-27714/00 | 11/2000 |
| DE | 44 32 947 A1 | 3/1996 |
| EP | 0129667 A1 | 1/1985 |
| EP | 0135172 A2 | 3/1985 |
| EP | 0136569 A2 | 4/1985 |
| EP | 0426998 A2 | 5/1991 |
| EP | 0 671 170 A1 | 9/1995 |
| EP | 0 795 553 A1 | 9/1997 |
| EP | 0 906 761 A2 | 4/1999 |
| FR | 2 693 724 | 1/1994 |
| GB | 1482238 | 8/1977 |
| GB | 1 495 189 A | 12/1977 |
| JP | S50-0035393 | 4/1975 |
| JP | S50-101360 A | 8/1975 |
| JP | S50-160483 A | 12/1975 |
| JP | S61-247396 A | 4/1986 |
| JP | S61-246124 A | 11/1986 |
| JP | S62-106016 A | 5/1987 |
| JP | S62-106017 A | 5/1987 |
| JP | S62-126186 A | 6/1987 |
| JP | H01-042427 A | 2/1989 |
| JP | H01-226824 A | 9/1989 |
| JP | H01-258669 A | 10/1989 |
| JP | H02-067218 A | 3/1990 |
| JP | H02-069165 A | 3/1990 |
| JP | H02-124883 A | 5/1990 |
| JP | H02-160722 A | 6/1990 |
| JP | H03-047049 A | 2/1991 |

| | | | |
|---|---|---|---|
| JP | H05-170756 A | 7/1993 |
| JP | H06-040876 A | 2/1994 |
| JP | H06-040909 A | 2/1994 |
| JP | H06-086682 A | 3/1994 |
| JP | H06-321752 A | 11/1994 |
| JP | H07-173148 A | 7/1995 |
| JP | H09-067362 A | 3/1997 |
| JP | H10-059956 A | 3/1998 |
| WO | WO 91/14429 A1 | 10/1991 |
| WO | WO 93/23069 | 11/1993 |
| WO | WO 94/23716 | 10/1994 |
| WO | WO 95/03293 A1 | 2/1995 |
| WO | WO 96/10341 A1 | 4/1996 |
| WO | WO 96/41800 A1 | 12/1996 |
| WO | WO 97/06273 A1 | 2/1997 |
| WO | WO 98/08503 A1 | 3/1998 |
| WO | WO 98/48790 A1 | 11/1998 |
| WO | WO 98/49153 A1 | 11/1998 |
| WO | WO 98/52546 A1 | 11/1998 |
| WO | WO 98/56373 | 12/1998 |
| WO | WO 99/11260 A1 | 3/1999 |
| WO | WO 99/11263 A1 | 3/1999 |
| WO | WO 99/18927 A1 | 4/1999 |
| WO | WO 99/18953 A1 | 4/1999 |
| WO | WO 99/36050 A1 | 7/1999 |
| WO | WO 99/37633 A1 | 7/1999 |
| WO | WO 99/43335 A1 | 9/1999 |
| WO | WO 00/03707 A1 | 1/2000 |
| WO | WO 00/16759 A2 | 3/2000 |
| WO | WO 00/54753 A2 | 9/2000 |
| WO | WO 00/62765 A2 | 10/2000 |
| WO | WO 00/64438 A1 | 11/2000 |
| WO | WO 00/66576 A1 | 11/2000 |

OTHER PUBLICATIONS

U.S. Appl. No. 09/546,565, filed Apr. 11, 2000, Kelly et al.
U.S. Appl. No. 09/602,191, filed Jun. 22, 2000, Kelly.
U.S. Appl. No. 09/889,701, filed Nov. 5, 2001, Heaton et al.
U.S. Appl. No. 09/986,509, filed Nov. 9, 2001, Kelly.
U.S. Appl. No. 10/176,762, filed Jun. 21, 2002, Kelly et al.
U.S. Appl. No. 10/177,387, filed Jun. 21, 2002, Kelly et al.
U.S. Appl. No. 10/181,549, filed Nov. 7, 2002, Husband et al.
U.S. Appl. No. 10/212,847, filed Aug. 5, 2002, Kelly et al.
U.S. Appl. No. 10/250,858, filed Jul. 9, 2003, Husband.
U.S. Appl. No. 10/274,371, filed Oct. 21, 2002, Kelly.
U.S. Appl. No. 10/459,537, filed Jun. 12, 2003, Kelly et al.
U.S. Appl. No. 10/469,957, filed Sep. 8, 2003, Husband et al.
U.S. Appl. No. 10/471,668, filed Sep. 15, 2003, Husband et al.
U.S. Appl. No. 10/600,004, filed Jun. 18, 2003, Kelly et al.
U.S. Appl. No. 10/611,087, filed Jul. 2, 2003, Kelly.
U.S. Appl. No. 10/611,151, filed Jul. 2, 2003, Kelly.
U.S. Appl. No. 10/636,902, filed Aug. 6, 2003, Kelly et al.
Adlercreutz, H. et al., "Determination of Urinary Lignans and Phytoestrogen Metabolites, Potential Antiestrogens and Anticarcinogens, in Urine of Women of Various Habitual Diets," *J. steroid Biochem.*, vol. 25, No. 58, pp. 791-797 (1986).
Adlercreutz, H. et al., "Effect of Dietary Components, Including Lignans and Phytoestrogens, on Enterohepatic Circulation and Liver Metabolism of Estrogens and on Sex Hormone Binding Globulin (SHBG)," *J. steroid Biochem*, vol. 27, No. 4-6, pp. 1135-1144 (1987).
Adlercreutz, H. et al., "Dietary Phytoestrogens and Cancer: In Vitro and In Vivo Studies," *J. Steroid Biochem. Molec. Bio.*, vol. 41, No. 3-8, pp. 331-337 (1992).
Adlercreutz, H. et al., "Dietary phyto-oestrogens and the menopause in Japan," *The Lancet*, vol. 339, pp. 1233, (May 1992).
Adlercreutz, H. et al., "Excretion of the Lignans Enterolactone and Enterodial and of Equol in Omnivorous and Vegetarian Postmenopausal Women and in Women with Breast Cancer," *The Lancet*, pp. 1295-1299, (Dec. 1982).
Adlercreutz, H., "Lignans and Phytoesrogens", *Front. gastrointest. Res.*, vol. 14, pp. 165-176, (1988).
Adlercreutz, H. et al., "Urinary excretion of lignans and isoflavonoid phytoestrogens in Japanese men and women consuming a traditional Japanese diet," *Am. J. Clin. Nutr.*, vol. 54, pp. 1093-1100, (1991).
Adlercreutz, H., "Western diet and Western diseases: some hormonal and biochemical mechanisms and associations," *Scand. J. Clin. Lab. Invest*, Suppl. 201, pp. 3-23, (1990).
Akkad, Andrea A. et al., "Abnormal Uterine Bleeding on Hormone Replacement: The Importance of Intrauterine Structural Abnormalities," *Obstetrics & Gynecology*, vol. 86, pp. 330-334 (1995).
Alegrio, L.V. et al.; "Diarylheptanoids and Isoflavonoids from *Centrolobium* Species"; Phytochemistry, vol. 28, No. 9, pp. 2359-2362, (1989).
Al-Maharik, N.I. et al., "Synthesis of C-C-Bridged Bis-Isoflavones," J. Org. Chem., vol. 65, pp. 2305-2308, (2000).
Anderson et al. "Biphasic Effects of Genistein on Bone Tissue in the Ovariectomized, Lactating Rat Model," P.S. E. B. M. vol. 217, pp. 345-350, (1998).
Anderson M.D., J. et al., "Meta-Analysis of the Effects of Soy Protein Intake on Serum Lipids," *New Eng. J. Med.*, vol. 333, No. 5, pp. 276-282, (Aug. 1995).
Baber, R. et al. "The effect of an isoflavone dietary supplement (Rismostil) on serum lipids, forearm bone density and endometrial thickness in post-menopausal women," Proc 10th *Annual Meeting of the North American Menopause Society*, New York, Sep. 23-25, 1999.
Bailey, E. T. et al., "Isoflavone Concentrations in the Leaves of the Species of the Genus *Trifolium*, Section *Calycomorphum*" Aust. J. agric. Res., vol. 22, No. 5, pp. 731-736, (Sep. 1971).
Bannerjee et al., "Polarography of Flavanone and Isoflavone", J. Electrochem. Soc. India, vol. 47, No. 4, pp. 237-244, (Oct. 1998).
Bannwart, C. et al., "Identification of the isoflavonic phytoestrogen daidzein in human urine," *Clinica Chemica Acta*, vol. 136, Nos. 2-3, pp. 165-172, (Jan. 1984).
Barnes, S. et al., "Soybeans Inhibit Mammary Tumors in Models of Breast Cancer," *Mutagens and Carcinogens in the Diet*, pp. 239-253, (1990).
Barrow, N.J., "Nutrient Potential and Capacity: II. Relationship between potassium potential and buffering capacity and the supply of potassium to plants," *Aust. J. Agric. Res.*, vol. 17, No. 6, pp. 849-861, (Nov. 1966).
Barrow, N.J. et al., "Nutrient Potential and Capacity: III: Minimum value of potassium potential for availability to *Trifolium subterraneum* in soil and in solution culture", *Aust. J. Agric. Res.*, vol. 18, pp. 55-62, (1967).
Beck, A.B., "The Oestrogenic Isoflavones of Subterranean Clover," *Aust. J. Agric. Res.*, vol. 15, pp. 223-230, (1964).
Beckham, N., "Estrogenic Activity in Plants—Summary of Talk by Nancy Beckham," from the Brisbane Seminar, 2 pgs., Jan. 1985.
Beckham, N., "Menopause," from *The Family Guide to Natural Therapies*, Greenhouse Publications, Richmond, pp. 41-42 and 50, (1988).
Beckham, N., "Herbal Help to Avoid Menopause Symptoms," *Australian Wellbeing*, No. 29, pp. 74-76, (1988).
Beckham, N., "Phyto-oestrogens and Comounds (sic) that Affect Oestrogen Metabolism—Part I," *Aust. J. Med. Herbalism*, vol. 7, No. 1, pp. 11-16, (1995).
Beckham, N., "Phyto-oestrogens and Compounds that Affect Oestrogen Metabolism—Part II," *Aust. J. Med. Herbalism*, vol. 7, No. 2, pp. 27-33, (1995).
Bennetts, H.W. et al., "A Specific Breeding Problem of Sheep on Subterranean Clover Pastures in Western Australia," *The Australian Veterinary Journal*, vol. 22, pp. 2-12, (Feb. 1946).
Beuker Velasse—Advertising Brochure—with English language translation, no date provided.
Beylot "Clinical signs of skin ageing." Revue Francaise de Gynecologie et d'Obstetrique, (1991) 86/6 (433-441) ISSN: 0035-290X.
Bezuidenhoudt, B.C.B. et al., "Synthesis of Isoflavanoid Oligomers Using a Pterocarpan as Inceptive Electrophile," J. Chem. Soc. Perkin Transactions I, pp. 2767-2778, 1991.
Bingham, S.A. et al., "Phyto-oestrogens: where are we now?," British Journal of Nutrition, vol. 79, pp. 393-406, 2001.

Bombardelli, E., "Chapter 7: Technologies for the Processing of Medicinal Plants," in *The Medicinal Plant Industry*, R.O.B. Wijesekera (Ed.), CRC Press LLC, New York, NY, pp. 85-98, (1991).

Bradbury, R.B. et al., "The Chemistry of Subterranean Clover. Part I. Isolation of Formononetin and Genistein," *J. Chem. Soc.*, pp. 3447-3449, (1951).

Bradbury, R.B. et al., "Estrogens and Related Substances in Plants," in *Vitamins and Hormones: Advances in Research and Applications* vol. XII, R.S. Harris et al. (Eds.), pp. 207-233, (1954).

Braden, A.W.H. et al., "Comparison of Plasma Phyto-Oestrogen Levels in Sheep and Cattle After Feeding of Fresh Clover," *Aust. J. agric. Res.*, vol. 22, pp. 663-670, (1971).

Braden, A.W.H. et al., "The Oestrogenic Activity and Metabolism of Certain Isoflavones in Sheep," *Aust. J. Agric. Res.*, vol. 18, pp. 335-348, (1967).

Bradley, P.R. (Ed.), "Contents" and "Index," in *British Herbal Compendium, Volume 1: A handbook of scientific information on widely used plant drugs*, British Herbal Medicine Association, Bournemouth, Dorset, pp. 5, 231-239, (1992).

Brandi, M.L., "Flavonoids: biochemical effects and therapeutic applications," *Bone and Mineral*, vol. 19 (Suppl.), pp. S3-S14, (1992).

Burali, C. et al., "Synthesis and Anti-Rhinovirus Activity of Halogen-Substituted Isoflavenes and Isoflavans," *European Journal of Medicinal Chemistry*, Editions Scientifique Elsevier, Paris, FR, 22(2):119-123 (Apr. 1987).

Buzzell, R.I. et al., "Inheritance of Flavonol Glycosides in Soybeans," *Can. J. Genet. Cytol.*, vol. 15, pp. 865-867, (1973).

Cassady, J.M. et al., Use of a Mammalian Cell Culture Benzo(a)pyrene Metabolism Assay for the Detection of Potential Anticarcinogens from Natural Products: Inhibition of Metabolism by Biochanin A, an Isoflavone from *Trifolium pratense* L, Cancer Research, vol. 48 (22), pp. 6257-6261, (Nov. 1998).

Caswell, A. (ed) "Hypolipidaemic Agent," MIMS Annual, 23rd edition, pp. 2-152 to 2-169, Singapore (1999).

Chan, K. et al., "Inhibitors of hydroxymethylglutaryl-coenzyme A reductase and risk of fracture among older women," *Lancet*; 355(9222):2185-8, Jun. 24, 2000.

Chang et al., "Metabolites of daidzein and genistein and their biological activities." Journal of Natural Products (1995), 58(12), pp. 1901-1905, ISSN: 0163-3864.

Chang Y., "Microwave-Mediated Synthesis of Anticarcinogenic Isoflavones from Soybeans," *J Argric Food Chem*. 1994, 42: 1869-1871.

Chicago Center for Clinical Research, Company Press Release Mar. 13, 2000, "Chicago Center for Clinical Research Study suggests New, More Effective Way to Treat Older Women with High Cholesterol".

Circle, S. J. et al., "Processing Soy Flours, Protein Concentrates, and Protein Isolates," in *Soybeans: Chemistry and Technology*, vol. 1: *Proteins*, A.K. Smith et al. (Eds.), Avi Publishing Company, Inc., Westport, CT, pp. 294-338, (1972).

Clifton-Bligh, P. et al., "The effect of isoflavones extracted from red clover (Rimostil) on lipid and bone metabolism," *Menopause* (in submission), pp. 1-27, 2000.

Collins, B.M. et al., "The estrogenic and antiestrogenic activities of phytochemicals with the human estrogen receptor expressed in yeast," *Steroids*, vol. 62, pp. 365-372, (Apr. 1997).

Coward, L. et al., "Genistein, Daidzein, and Their Ǝ-Glycoside Conjugates: Antitumor Isoflavones in Soybean Foods from American and Asain Diets," *Agric. Food Chem.*, vol. 41, No. 11, pp. 1961-1967, (Nov. 1993).

Culbreth, David M.R. (Ed.), *Manual of Materia Medica and Pharmacology*, Eclectic Medical Publications, Portland, OR, pp. 19-22, (1922).

Davies, H.L. et al., "Further Studies on Oestrogenic Activity in Strains of Subterranean Clover (*Trifolium Subterraneum* L.) In South-Western Australia," *Aust. J. Agric. Res.* vol. 16, No. 6, pp. 937-950, (Nov. 1965).

Davis, H. et al., "Extraction," from *Bentley's Text-Book of Pharmaceuticals*, 6th ed., Chapter XVIII, pp. 272-273, (1956).

Deschamps-Vallet, C. et al., "Transformation Du Cation Isoflavylium en Phenyl-3 Coumarines, Isoflavenes-3 et Isoflavannes," *Tetrahedron Letters*, 24(37):3993-3996 (1983).

Dewick, P.M. "5: Isoflavonoids,", *The Flavonoids: Advances in Research Since 1986*, Ed. by J. B. Harborne, Published by Chapman & Hall, London, pp. 117-138.

Doren, M. et al., "Identification and Treatment of Postmenopausal Women at Risk for the Development of Osteoporosis," *International Journal of Clinical Pharmacology, Therapy and Toxicology*, vol. 20, No. 11, pp. 431-433 (1992).

Dubey et al. "Phytoestrogens Inhibit Growth and MAP Kinase Activity in Human Aortic Smooth Muscle Cells," *Hypertension*, vol. 33 (part II), pp. 177-182, (1999).

Düker, E. et al., "Effects of Extracts from *Cimicifuga racemosa* on Gonadotropin Release in Menopausal Women and Ovariectomized Rats," *Planta Med.*, vol. 57, pp. 420-424, (1991).

Eldridge, A.C., "Determination of Isoflavones in Soybean Flours, Protein Concentrates, and Isolates," *J. Agric. Food. Chem.*, vol. 30, No. 2, pp. 353-355, (1982).

Eldridge, A.C., "High-performance liquid chromatography separation of soybean isoflavones and their glucosides," *J. Chromatography*, vol. 234 pp. 494-496, (1982).

Eldridge, A.C. et al., "Soybean Isoflavones: Effect of Environment and Variety on Composition," *J. Agric. Food Chem.*, vol. 31 pp. 394-396, (1983).

Ellis, G.P. (ed.); "Chromenes, Chromanones, and Chromones"; pp. 256-260; published by John Wiley & Sons, 1977.

EPO Communication dated Mar. 8, 2002 issued for Application No. EP 93 909 679.8.

EPO Supplemental Partial Search Report issued for Application No. EP 99 91 2976.

Evans, D. et al., "Ovarian Cancer Family and Prophylactic Choices," *Journal of Medical Genetics*, pp. 416-418, 1991.

Evans, M. et al., "Hormone Replacement Therapy: Management of Common Problems," Mayo Clin. Proc, vol. 70, pp. 800-805, (1995).

Fanti et al. "The Phytoestrogen Genistein Reduces Bone Loss in Short-Term Ovariectomized Rats," *Osteoporosis Int.*, vol. 8, pp. 274-281, (1998).

Farmakalidis, E. et al., "Isolation of 6"-O-Acetylgenistin and 6"-O-Acetyldaidzin from Toasted Defatted Soyflakes," *J. Agric. Food Chem.*, vol. 33, pp. 385-389, (1985).

Farmakalidis, E. et al., "Semi-preparative high-performance liquid chromatographic isolation of soybean isoflavones," *J. Chromatography*, vol. 295, pp. 510-514, (Jul. 1984).

Farnsworth, N.R. et al., "Potential Value of Plants as Sources of New Antifertility Agents II," *J. Pharm. Sciences*, vol. 64, No. 5, pp. 717-753, (May 1975).

Francis., C.M. et al., "The Distribution of Oestrogenic Isoflavones in the Genus *Trifolium,*" *Aust. J. Agric. Res.*, 18(1):47-54, (Jan. 1967).

Francis, C.M. et al., "Varietal Variation in the Isoflavone Content of Subterranean Clover: Its Estimation by a Microtechnique," *Aust. J. Agric. Res.*, vol. 16, No. 4, pp. 557-564, (Jul. 1965).

Gaynor, J.D. et al., "HPLC Separation and Relative Quantitation of Kaempferol Glycosides in Soybean," *Chromatographia*, vol. 25, No. 12, pp. 1049-1053, (Dec. 1988).

Gildersleeve, R.R. et al., "Screening Rose Clover and Subterranean Clover Germplasm for Isoflavones," *Crop. Sci.*, vol. 31, No. 5, pp. 1374-1376, (Sep.-Oct. 1991).

Gildersleeve, R.R. et al., "Detection of Isoflavones in Seedling Subterranean Clover," *Crop Sci.*, vol. 31, pp. 889-892, (Jul.-Aug. 1991).

Gladstones, J.S., "Naturalized Subterranean Clover Strains in Western Australia: A Preliminary Agronomic Examination," *Aust. J. agric. Res.*, vol. 18, No. 5, pp. 713-731, (Sep. 1967).

Goh, J.T.W. et al., "Postmenopausal Endometrioma and Hormonal Replacement Therapy," *Aust NZ J. Obstet Gynaecol*, vol. 32, pp. 384-385 (1992).

Graham, T. L., "Flavonoid and Isoflavonoid Distribution in Developing Soybean Seedling Tissues and in Seed and Root Exudates," *Pharm. Physiol.* vol. 95, pp. 594-603, (1991).

Grodstein, F., et al., "Postmenopausal Hormone Use and Cholecystectomy in a Large Prospective Study," *Obstetrics & Gynecology*, vol. 83, No. 1, pp. 5-11 (1994).

Grunert E. et al., "Isoflavone in einigen Weiß- und Rotkleesorten und ihre oestrogene Wirksamkeit bei juvenilen Mäusen," Deutsche Tierärztliche Wochenschrift, 74. Jahrgang 1967, pp. 431-433.

Hebert, P. et al., (1997), "Cholesterol lowering with statin drugs, risk of stroke, and total mortality. An overview of randomized trials," JAMA 278(4):313-21.

Herman, C. et al., "Soybean Phytoestrogen Intake and Cancer Risk," *American Institute of Nutrition*, pp. 757S-770S, (1995).

Hodgson, J. et al., (1998), "Supplementation with isoflavonoid phytoestrogens does not alter serum lipid concentrations: a randomised controlled trial in humans," Journal of Nutrition, 128: 728-332.

Holt, S., "Selected Bibliography of Scientific Studies on Genistein and Other Soya Isoflavones," Soya for Health: The Definitive Medical Guide, Mary Ann Liebert, Inc., Larchmont, NY, pp. 159-170, (1996).

Hulley, S. et al., (1998), "Randomized trial of estrogen plus progestin for secondary prevention of coronary heart disease in postmenopausal women," JAMA 280(7):605-613.

Inoue, N., 1964, "Studies of Synthetic Isoflavones. V. The Reduction of Isoflavone," originally from *Bull. Chem. Soc. Japan*, May 1964, 37(5): 601-605, cited in *STN International, CAPLUS database*, (Columbus, Ohio), No. 61: 32297 (2 pages).

Jenkins, D.J.A. et al., "Leguminous seeds in the dietary management of hyperlipidemia," *Am. J. Clin. Nut.*, vol. 38, pp. 567-573, (1983).

Joannou, G.E. et al., "A Urinary Profile Study of Dietary Phytoestrogens. The Identification and Mode of Metabolism of New Isoflavonoids," *J. Steroid Biochem. Molec. Biol.*, vol. 54, No. 3/4, pp. 167-184, (1995).

Jones, A.E. et al., "Development and Application of a High-performance Liquid Chromatographic Method for the Analysis of Phytoestrogens," *J. Sci. Food Agric.*, vol. 46, pp. 357-364, (1989).

Jurd, L. et al.; "Phenolic and Quinoidal Constituents of Dalbergia Retusa," Tetrahedron Letters, vol. 21, pp. 2149-2152; (1972).

Kaldas, R.S. et al., "Reproductive and General Metabolic Effects of Phytoestrogens in Mammals," *Reproductive Toxicology*, vol. 3, No. 2, pp. 81-89, (1989).

Kao, Y., et al., "Molecular Basis of the Inhibition of Human Aromatase (Estrogen Synthetase) by Flavone and Isoflavone Phytoestrogens: A Site-directed Mutagenesis Study," *Environmental Health Perspectives*, vol. 106, No. 2, pp. 85-92 (1998).

Kelly et al., "Metabolites of dietary (soya) isoflavones in human urine," Clinica Chimica Acta 223(1-2), pp. 9-22 (Dec. 31, 1993).

Kelly, S. A. et al., "Protein Tyrosine Phosphorylation Mediates TNF-Induced Endothelial-Neutrophil Adhesion in Vitro", The American Physiological Society, 274 (2Pt2), pp. H513-H519, (1998).

Kelly, G. et al., "Standardized Red Clover Extract Clinical Monograph," Natural Products Research Consultants, Inc., Seatle, WA, pp. 3-12, (1998).

Kitada, Y. et al., "Determination of isoflavones in soy bean by high performance liquid chromatography with amperometric detection," *J. Chromatography*, vol. 366, pp. 403-406, (1986).

Kitts, D.D. et al., "Uterine Weight Changes and $^3$H-Uridine Uptake in Rats Treated with Phytoestrogens," *Can. J. Anim. Sci.*, vol. 60, pp. 531-534, (Jun. 1980).

Knuckles, B.E. et al., "Coumestrol Content of Fractions Obtained during Wet Processing of Alfalfa," *J. Agric. Food Chem.*, vol. 24, No. 6, pp. 1177-1180, (Nov.-Dec. 1976).

Kudou, S et al., "A New Isoflavone Glycoside in Soybean Seeds (*Glycine max* Merrill), Glycitein 7-*O*- β- D-(6"-*O*-Acetyl)-Glucopyranoside," *Agric. Biol. Chem.*, vol. 55, No. 3, pp. 859-860, (1991).

Kudou, S. et al., "Malonyl Isoflavone Glycosides in Soybean Seeds (*Glycine max* Merrill)," *Agric. Biol. Chem.*, vol. 55, No. 9, pp. 2227-2233, (1991).

Lamberton, et al., "Catalytic Hydrogenation of Isoflavones. the Preparation of (±)-Equol and Related Isoflavans", Aust. J. Chem. vol. 31, pp. 455-457, (Feb. 1978).

Liepa, A.J. "A Synthesis of Hydroxylated Isoflavylium Salts and Their Reduction Products", Aust. J. Chem., vol. 34, pp. 2647-2655, (1981).

Lindner, H.R., "Study of the Fate of Phyto-Oestrogens in the Sheep by Determination of Isoflavones and Coumestrol in the Plasma and Adipose Tissue," *Aust. J. Agric. Res.*, vol. 18, pp. 305-333, (1967).

Lindner, H.R., "V/1 Occurrence of Anabolic Agents in Plants and their Importance," Environmental Quality and Safety Supplement, Thieme, Stuttgart, Germany, 1976, 5: 151-158.

Liu, Y. et al., "Abstract No. 78763p; Effects of solid dispersion of diadzein on the blood pressure of spontaneously hypersensitive rats," Chemical Abstracts, vol. 115, No. 8, p. 466 (Aug. 26, 1991).

Lock, M., "Contested meanings of the menopause," *The Lancet*, vol. 337, pp. 1270-1272, (May 25, 1991).

Mäkelä, S., et al., "Inhibition of 17β-Hydroxysteroid Oxidoreductase by Flavonoids in Breast and Prostate Cancer Cells," pp. 310-316 (1998).

Martin, P.M. et al., "Phytoestrogen Interaction with Estrogen Receptors in Human Breast Cancer Cells," *Edocrinology*, vol. 103, No. 5, pp. 1860-1867, (1978).

May, M. J. et al., "Effects of Protein Tyrosine Kinase Inhibitors on Cytokine-Induced Adhesion Molecule Expression by Human Umbilical Vein Endothelial Cells", British Journal of Pharmacology, No. 118, pp. 1761-1771, (1996).

Mazur et al.; "Natural and anthropogenic environmental oestrogens: the scientific basis for risk assessment -Naturally occurring oestrogens in food," Pure & Appl. Chem. 70(9), pp. 1759-1776 (1998).

Mazur et al., "Isolfavonoids and lignans in legumes: Nutritional and health aspects in humans," Nutritional Biochemistry 9, pp. 193-200 (1998).

The Merck Index, 8$^{th}$ Ed., "Daidzein," "Formononetin," and "Geinstein," pp. 320, 484, and 469-470 [respectively], Merck and Co., Inc., (1968).

Messina, M. et al., "The Role of Soy Products in Reducing Risk of Cancer," *J. of National Cancer Institute*, vol. 83, No. 8, pp. 541-546, (Apr. 17, 1991).

Morris, P. et al., "Identification and accumulation of isoflavonoids and isoflavone glucosides in soybean leaves and hypocotyls in resistance responses to *Phytophthora megasperma* f.sp. *glycinea*," *Physiological and Molecular Plant Pathology*, vol. 39, pp. 229-244, (1991).

Mowrey, D.B., "Introduction," in *Next Generation Herbal Medicine: Guaranteed Potency Herbs*, 2$^{nd}$ Edition, Keats Publishing, Inc., New Canaan, CT, pp. 3-13, (Jan. 1990).

Murphy, P.A., "Phytoestrogen Content of Processed Soybean Products," *Food Technology*, pp. 60-64, (Jan. 1982).

Murphy, P.A., "Separation of genistin, daidzin and their aglucones, and coumesterol by gradient high-performance liquid chromatography," *J. Chromatography*, vol. 211, No. 1, pp. 166-169, (1981).

Naim, M. et al., "A New Isoflavone from Soya Beans," *Phytochemistry*, vol. 12, pp. 169-170, (1973).

Naim, M., "The Isolation, Characterization and Biological Activity of Isoflavones from Soybeans," Submitted to the Senate of the Hebrew University of Jerusalem—Oct. 1974.

Naim, M. et al., "Soybean Isoflavones. Characterization, Determination, and Antifungal Activity," *J. Agr. Food Chem.*, vol. 22, No. 5, pp. 806-810, (1974).

Namnoum, A.B., et al., "Incidence of symptom recurrence after hysterectomy for endometriosis," *Fertility and Sterility*, vol. 64, No. 5, pp. 898-902 (1995).

Nash, A.M. et al., "Fractionation and Characterization of Alcohol Extractables Associated with Soybean Proteins. Nonprotein Components," *J. Agr. Food Chem.*, vol. 15, No. 1, pp. 102-108, (Jan.-Feb. 1967).

Nestel, P. et al., (1997), "Soy isoflavones improve systemic arterial compliance but not plasma lipids in menopausal and peri-menopausal women," *Arteriosclerosis, Thrombosis and Vascular Biology* 17: 3392-3398.

Nestel, P. et al., (1999), "Isoflavones from red clover improves systemic arterial compliance but not plasma lipids in menopausal women," Journal of Clinical Endocrinology and Metabolism 84: 895-898.

Ohta, N. et al., "Isoflavonoid Constituents of Soybeans and Isolation of a New Acetyl Daidzin," *Agric. Biol. Chem.*, vol. 43, No. 7, pp. 1415-1419, (1979).

Okano, K. et al., "Isolation of Four Kinds of Isoflavon from Soya Bean (abstract),"*Bull. Agr. Chem. Soc. Japan*, vol. 15, Nos. 172-183p. 110, (1939).

Okubo, K. et al., "Components Responsible for the Undesirable Taste of Soybean Seeds," *Biosci. Biotech. Biochem.*, vol. 56, No. 1, pp. 99-103, (1992).

Palmetshofer, A. et al., "α-Galactosyl Epitope-Mediated Activation of Porcine Aortic Endothelial Cells", Transplantation, vol. 65, No. 7, pp. 971-978, (Apr. 15, 1998).

Panchagnula, R. et al., "Transdermal iontophoresis revisited," Curr. Opin. Chem. Biol, Aug. 2000; 4(4):468-73.

Parfitt, K., Martindale 32nd edition, "The complete drug reference," (1999), 32nd Edition,. Pharmaceutical Press, London, pp. v. and vi.

PCT Search Report issued for Application No. PCT/AU00/01056 dated Nov. 27, 2000.

Peterson, G. et al., "Genistein and Biochanin A Inhibit the Growth of Human Prostate Cancer Cells but not Epidermal Growth Factor Receptor Tyrosine Autophosphorylation," *The Prostate*, vol. 22, No. 4, pp. 335-345, (1993).

Peterson, G. et al., "Genistein Inhibition of the Growth of Human Breast Cancer Cells: Independence From Estrogen Receptors and the Multi-drug Resistance Gene," *Biochemical and Biophysical Research Communications*, vol. 179, No. 1, pp. 661-667, (Aug. 1991).

Pope, G.S., "The Importance of Pasture Plant Oestrogens in the Reproduction and Lactation of Grazing Animals," *Dairy Science Abstracts*, vol. 16, No. 5, pp. 333-356, (May 1954).

Potter, S. et al., (1998), "Soy protein and isoflavones: their effect on blood lipids and bone density in postmenopausal women," American Journal of Clinical Nutrition, 68(Suppl):1375S-1379S.

Price, K.R. et al., "Naturally occurring oestrogens in foods—A review," *Food Additives and Contaminants*, vol. 2, No. 2, pp. 73-106, (1985).

Reinli, K. et al., "Phytoestrogen Content of Foods—A Compendium of Literature Values," *Nutrition and Cancer*, vol. 26, No. 2, pp. 123-148, (1996).

Rose, D.P., "Dietary Fiber, Phytoestrogens, and Breast Cancer," *Nutrition*, vol. 8, No. 1, pp. 47-51, (Jan.-Feb. 1992).

Rossiter, R.C. et al., "Physiological and Ecological Studies on the Oestrogenic Isoflavones in Subterranean Clover (*T. subterraneum* L.), III: Effects of Light" *Aust. J. Agric. Res.*, vol. 18, No. 1, 23-27, (Jan. 1967).

Rossiter, R.C., "Physiological and Ecological Studies on the Oestrogenic Isoflavones in Subterranean Clover (*T. subterraneum* L.), IV: Effects of Zinc Deficiency in Clover Seedlings," *Aust. J. Agric. Res.*, vol. 18, No. 1, 39-46, (Jan. 1967).

Sacks, F. et al., (1996), "The effect of pravastatin on coronary events after myocardial infarction in patients with average cholesterol levels," Cholesterol and Recurrent Events Trial Investigators, New England Journal of Medicine, 335(14):1001-9.

Samman, S. et al., (1999), "The effect of supplementation with isoflavones on plasma lipids and oxidisability of low density lipoprotein in pre-menopausal women," Atherosclerosis 147:277-283.

Sanchez-Guerrero, J. et al., "Postmenopausal Estrogen Therapy and the Risk for Developing Systemic Lupus Erythematosus," *Annals of Internal Medicine*, vol. 122, No. 6, pp. 430-433 (1995).

Sbarouni, E. et al., (1998), "The effect of hormone replacement therapy alone and in combination with simvastatin on plasma lipids of hypercholesterolemic postmenopausal women with coronary artery disease," Journal of the American College of Cardiology 32(5): 122-50.

Scandinavian Simvastation Survival Study Group, (1994), "Randomised trial of cholesterol lowering in 4444 patients with coronary heart disease: the Scandinavian Simvastatin Survival Study (4S)," Lancet 344:1383-89.

Schultz, "Isoflavonglucoside Formononetin-7-glucosid und Biochanin A-7-glucosid in Trifolium pratense L.," Die Naturwissenschaften, 52(18), p. 517, Sep. 1965.

Sener, A.B., et al., "The effects of hormone replacement therapy on uterine fibroids in postmenopausal women," *Fertility and Sterility*, vol. 65, No. 2, pp. 354-357 (1996).

Seo, A. et al., "Improved High-Performance Liquid Chromatographic Analysis of Phenolic Acids and Isoflavonoids from Soybean Protein Products," *J. Agric. Food Chem.*, vol. 32, No. 3, pp. 530-533, (1984).

Setchell, K.D.R. et al., "High-Performance Liquid Chromatographic Analysis of Phytoestrogens in Soy Protein Preparations with Ultraviolet, Electrochemical and Thermospray Mass Spectrometric Detection," *J. Chromatography*, vol. 386 pp. 315-345, (1987).

Setchell, K.D.R. et al., "14: Mammalian Lignans and Phytooestrogens Recent Studies on their Formation, Metabolism and Biological Role in Health and Disease," in *Role of the Gut Flora in Toxicity and Cancer*, I.R. Rowland (Ed.), Academic Press, Inc., San Diego, CA, pp. 315-339, (1988).

Setchell, K.D.R. et al., "Nonsteroidal estrogens of dietary origin: possible roles in hormone-dependent disease," *Am. J. Clin. Nut.*, vol. 40, pp. 569-578, (1984).

Sharma, R.D., "Effect of Various Isoflavones on Lipid Levels in Triton-treated Rats," Atherosclerosis 33, 1979, p. 371-375.

Shimoyamada, M. et al., "Saponin Composition in Developing Soybean Seed (*Glycine max* (L) Merrill, cv. Mikuriyaao)," *Agric. Biol. Chem.*, vol. 55, No. 5, pp. 1403-1405, (May 1991).

Shutt, Donald A., "The effects of plant oestrogens on animal reproduction," *Endeavour*, vol. 35, pp. 110-113, (1976).

Shutt, D.A. et al., "Free and Conjugated Isoflavones in the Plasma of Sheep Followed Ingestion of Oestrogenic Clover," *Aust. J. agric. Res.*, vol. 18, pp. 647-655, (1967).

Shutt, D.A., "Interaction of Genistein With Oestradiol in the Reproductive Tract of the Ovariectomized Mouse," *J. Endrocrin.*, vol. 37, pp. 231-232, (1967).

Shutt, D.A. et al., "Quantitative Aspects of Phyto-Oestrogen Metabolism in Sheep Fed on Subterranean Clover (*Trifolium subterraneum* Cultivar Clare) or Red Clover (*Trifolium pratense*)," *Aust. J. agric. Res.*, vol. 21, pp. 713-722, (1970).

Shutt, D.A. et al., "The Significance of Equol in Relation to the Oestrogenic Responses in Sheep Ingesting Clover with a High Formononetin Content," *Aust. J. agric. Res.*, vol. 19, pp. 545-553, (1968).

Shutt, D.A. et al., "Steroid and Phyto-Oestrogen Binding to Sheep Uterine Receptors In Vitro," *J. Endocr.*, vol. 52, pp. 299-310, (1972).

Siddiqui et al. "Hypolipidemic principles of *Cicer arietinum*: Biochanin-A and Formononetin," Lipids, vol. 11, No. 3, pp. 243-246, (1975).

Smith, A.K. et al. (Eds.), "Solvent Treatment of Beans and Fractions," in *Soybeans: Chemistry and Technology* vol. 1: Proteins, Avi Publishing Co., Inc., Westport, CT, p. 149, (1972).

Smith, A.K. et al. (Eds.), "Phenolic Constituents," in *Soybeans: Chemistry and Technology vol. 1: Proteins*, Avi Publishing Co., Inc., Westport, CT, pp. 187-189, (1972).

Smith, G.R. et al., "Influence of Harvest Date, Cultivar, and Sample Storage Method on Concentration of isoflavones in Subterranean Clover," *Crop Science*, vol. 26, No. 5, pp. 1013-1016, (Sep.-Oct. 1986).

Stampfer, M. et al., "A Prospective Study of Cholesterol, Apolipoproteins, and the Risk of Myocardial Infarction," *The New England Journal of Medicine*, vol. 325, No. 6, pp. 373-381, (1991).

Statutory Declaration of Fiona Bathgate, declared Mar. 24, 1998, 4 pages.

Amended Statutory Declaration of Fiona Bathgate, declared Oct. 26, 1998, 2 pages.

Statutory Declaration of Nancy Beckham, declared Sep. 8, 1998, 20 pages.

Statutory Declaration of Kerry Martin Bone, declared Oct. 5, 1998, 31 pages.

Statutory Declaration of Jennifer Carpinelli, declared Oct. 21, 1998, 2 pages.

Statutory Declaration of G. Clements, declared Jan. 27, 1999, 2 pages.

Statutory Declaration of Julie Hill, declared Apr. 4, 1998, 2 pages.

Statutory Declaration of Norbert Krause, declared Nov. 5, 1998, 23 pages.

Statutory Declaration of Ngaire Petit-Young, declared Nov. 5, 1998, 3 pages.

Statutory Declaration of Hubert Regtop, declared Nov. 24, 1998, 53 pages.
Statutory Declaration of Joseph Nicolas Van Haaster, declared Jan. 26, 1999, including Exhibit "JNVH-1," 20 pages.
Szabo et al., 1973, "The Selective Reduction of Isoflavon," *Tetrahedron Letters*, 19: 1659-1662.
Trease, G.E. et al., "20: Introduction and General Methods," in *Pharmacognosy, 12th edition*, Bailliére Tindall, Alden Press, Oxford, Great Britain, pp. 241-260, (1983).
Troisi, R.J., et al., "Menopause, Postmenopausal Estrogen Preparations and the Risk of Adult-Onset Asthma," *Am J Respir Crit Care Med*, vol. 152, pp. 1183-1188 (1995).
Verdeal, K. et al., "Naturally-Occurring Estrogens in Plant Foodstuffs—A Review," *J. Food Protect.*, vol. 42, No. 7, pp. 577-583 (Jul. 1979).
Wähälä, K. et al., "Hydrogen Transfer Reduction of Isoflavones," *Heterocycles*, 28(1):183-186 (1989).
Walter, E.D., "Genistin (an Isoflavone Glucoside) and its Aglucone, Genistein, from Soybeans," *J. Am. Chem. Soc.*, vol. 63, pp. 3273-3276, (Jul.-Dec. 1941).
Walz, E., "Isoflavon- und Saponin-Glucoside in Soja hispida," Justus Liebigs Annalen der Chemie., vol. 489, pp. 118-155 (1931).
Wang, C., et al., "Phytoestrogen Concentration Determines Effects on DNA Synthesis in Human Breast Cancer Cells," *Nutrition and Cancer*, 28(3), pp. 236-247, (1997).
Wang, G. et al., "A Simplified HPLC Method for Determination of Phytoestrogens in Soybean and its Processed Products," *J. Agr. Food Chem.*, vol. 38, No. 1, pp. 185-190 (1990).
Weber, C., "Involvement of Tyrosine Phosphorylation in Endothelial Adhesion Molecule Induction", Immunologic Research, No. 15, pp. 30-37, (1996).
Weidenbörner, M., et al., "Antifungal Activity Of Isoflavonoids In Different Reduced Stages On *Rhizoctonia solani* and *Sclerotium rolfsh*", Phytochemistry, Vo. 29, No. 3, pp. 801-803, (1990).
Weinberg, D.S. et al., "Identification and Quantification of Anticarcinogens in Garlic Extract and Licorice Root Extract Powder," Journal of High Resolution Chromatography, vol. 15, Oct. 1992, p. 641-654.
Welshons, W.V. et al., "Stimulation of breast cancer cells in vitro by the environmental estrogen enterolactone and the phytoestrogen equol," *Breast Cancer Research and Treatment*, vol. 10, 169-175, (1987).
Whalley, W.B.; "5:4'-Dihydroxy-8-Methyl*iso*flavone, and a Note on Lotoflavin," Journal of the Chemical Society, pp. 1833-1837, (1957).
White, E. et al., "Extracta," in *Pharmacopedia; A Commentary on the British Pharmacopoeia, 1898, 2nd Edition*, Simpkin, Marshall, Hamilton, Kent & Co., Ltd., London, England, pp. 166-167, (1909).
Wilcox, G. et al., "Oestrogenic effects of plant foods in postmenopausal women," *British Med. J.*, vol. 301, pp. 905-906, (Oct. 20, 1990).
Winship, K.A., "Unopposed estrogens," Adv. Drug React. Ac. Pois. Rev., vol. 1, pp. 37-66, (1987).
Wong, E., "Detection and Estimation of Oestrogenic Constituents in Red Clover," *J. Sci. Food Agric.*, vol. 13, pp. 304-308, (May 1962).
Wong, E. et al., "The Oestrogenic Activity of Red Clover Isoflavones and some of Their Degradation Products," *J. Endocrin.*, vol. 24, pp. 341-348, (1962).
Yahara, S. et al., "Isoflavan and Related Compounds from *Dalbergia odorifera*. 1" Chem, Pharm. Bull. 37(4):979-987 (Apr. 1989).
Widyarini et al., "Isoflavonoid Compounds from Red Clover (*Trifolium pratense*) protect from Inflammation and Immune Suppression Induced by UV Radiation," *Photochem. Photobiol.* 74(3):465-470 (2001).
International Search Report for PCT/AU00/01056, dated Nov. 27, 2000, 5 pages.
Supplementary Partial European Search Report for EP Appl. No. 00 96 0231, dated Apr. 15, 2003, 3 pages.
EPO Examination Report for EP Appl. No. 00 96 0231, dated Jul. 31, 2003, 4 pages.
Technical Report by Novogen, Inc., 5 pages, submitted in connection with a Response to an EP Communication dated May 17, 2005.
Farkas, L. et al., "Synthesis of sophorol, violanone, lonchocarpan, claussequinone, philenopteran, leiocalycin, and some other natural isoflavonoids by the oxidative rearrangement of chalcones with thallium(III) nitrate," *J. Chem. Soc. Perkin I*, pp. 305-312 (1974).
Krishnamurty, H. & Sathyanarayana, S., "Catalytic transfer hydrogenation, a chemo-selective reduction of isoflavones to isoflavanones," *Synth. Commun.* 16(13):1657-1663 (1986).
Visser, F. & Lane, G., "Selectivity of the hydrogenation of 2',4',7-tribenzyloxyisoflavone," *Aust. J. Chem.* 40:1705-1711 (1987).
Statutory Declaration of Fiona Bathgate (Amended), declared Oct. 26, 1998, 2 pages.
Statutory Declaration of Fiona Bathgate, declared Mar. 24, 1998, 4 pages.
Statutory Declaration of G. Clements, declared Jan. 27, 1999, 2 pages.
Statutory Declaration of Hubert Regtop, declared Nov. 24, 1998, 53 pages.
Statutory Declaration of Jennifer Carpinelli, declared Oct. 21, 1998, 2 pages.
Statutory Declaration of Joseph Nicolas Van Haaster, declared Jan. 26, 1999, including Exhibit "JNVH-1," 20 pages.
Statutory Declaration of Julie Hill, declared Apr. 4, 1998, 2 pages.
Statutory Declaration of Kerry Martin Bone, declared Oct. 5, 1998, 31 pages.
Statutory Declaration of Nancy Beckham, declared Sep. 8, 1998, 20 pages.
Statutory Declaration of Ngaire Petit-Young, declared Nov. 5, 1998, 3 pages.
Statutory Declaration of Norbert Krause, declared Nov. 5, 1998, 23 pages.
Office Action in U.S. Patent No. 6,649,648 (U.S. Appl. No. 09/254,026) dated Oct. 23, 2001.
Amendment filed in U.S. Patent No. 6,649,648 (U.S. Appl. No. 09/254,026) dated Apr. 23, 2002.
Amended Amendment filed in U.S. Patent No. 6,649,648 (U.S. Appl. No. 09/254,026) dated Aug. 8, 2002.
Amendment filed in U.S. Patent No. 6,649,648 (U.S. Appl. No. 09/254,026) dated Nov. 27, 2002.
Amendment filed in U.S. Patent No. 6,649,648 (U.S. Appl. No. 09/254,026) dated Feb. 21, 2003.
Notice of Allowance with Reasons for Allowance in U.S. Patent No. 6,649,648 (Appl. No. 09/254,026) dated May 6, 2003.
Office Action in U.S. Appl. No. 10/176,762 dated May 21, 2003.
Reply to Office Action filed in U.S. Appl. No. 10/176,762 dated Aug. 21, 2003.
Office Action in U.S. Appl. No. 10/176,762 dated Nov. 4, 2003.
Amendment filed in U.S. Appl. No. 10/176,762 dated May 4, 2004.
Amendment filed in U.S. Appl. No. 10/176,762 dated Jun. 25, 2004.
Office Action in U.S. Appl. No. 10/176,762 dated Sep. 28, 2004.
Amendment and Response filed in U.S. Appl. No. 10/176,762 dated Mar. 25, 2005.
Office Action in U.S. Appl. No. 10/176,762 dated Jun. 29, 2005.
Response to Office Action filed in U.S. Appl. No. 10/176,762 on Dec. 29, 2005.
Office Action issued in U.S. Appl. No. 10/176,762 on Apr. 14, 2006.
Preliminary Amendment filed in U.S. Appl. No. 10/177,387 dated Jun. 21, 2002.
Office Action in U.S. Appl. No. 10/177,387 dated Mar. 25, 2003.
Reply to Office Action filed in U.S. Appl. No. 10/177,387 dated Sep. 24, 2003.
Office Action in U.S. Appl. No. 10/177,387 dated Dec. 18, 2003.
Reply to Final Office Action filed in U.S. Appl. No. 10/177,387 dated Jun. 18, 2004.
Advisory Action in U.S. Appl. No. 10/177,387 dated Jul. 8, 2004.
Amendment filed in U.S. Appl. No. 10/177,387 dated Nov. 18, 2004.
Office Action in U.S. Appl. No. 10/177,387 dated Feb. 17, 2005.
Response to Office Action filed in U.S. Appl. No. 10/177,387 dated Aug. 16, 2005.
Office Action in U.S. Appl. No. 10/177,387 dated Nov. 2, 2005.
Preliminary Amendment filed in U.S. Appl. No. 10/636,902 dated Aug. 6, 2003.
Preliminary Amendment filed in U.S. Appl. No. 11/024,512 dated Dec. 28, 2004.
Preliminary Amendment filed in U.S. Appl. No. 11/415,950 on May 1, 2006.

Office Action in U.S. Patent No. 6,455,032 (U.S. Appl. No. 09/582,317) dated Aug. 1, 2001.
Response filed in U.S. Patent No. 6,455,032 (U.S. Appl. No. 09/582,317) dated Feb. 1, 2002.
Office Action in U.S. Appl. No. 10/212,847 dated Aug. 13, 2003.
Response to Office Action filed in U.S. Appl. No. 10/212,847 dated Jan. 13, 2004.
Office Action in U.S. Appl. No. 10/212,847 dated Apr. 21, 2004.
Response to Office Action filed in U.S. Appl. No. 10/600,004 dated Oct. 13, 2005.
Preliminary Amendment filed in U.S. Appl. No. 10/947,356 dated Sep. 21, 2004.
Office Action mailed in U.S. Appl. No. 10/851,270 on Jun. 9, 2006.
Preliminary Amendment filed in U.S. Appl. No. 11/442,369 on May 25, 2006.
Office Action in U.S. Appl. No. 10/070,361 dated May 7, 2003.
Office Action in U.S. Appl. No. 10/181,549 dated Nov. 16, 2004.
Response to Office Action filed in U.S. Appl. No. 10/181,549 dated May 16, 2005.
Office Action in U.S. Appl. No. 10/181,549 dated Nov. 2, 2005.
Preliminary Amendment filed in U.S. Appl. No. 10/250,858 dated Dec. 1, 2004.
Preliminary Amendment filed in U.S. Appl. No. 10/471,668 dated Jun. 16, 2004.
Preliminary Amendment filed in U.S. Appl. No. 10/493,390 dated Mar. 16, 2005.
Wähälä, K. et al., "Synthesis and Labeling of Isoflavone Phytoestrogens, Including Daldzeln and Genistein," *Proceedings Of The Society For Experimental Biology And Medicine*, 208(1):27-32 (1995).

\* cited by examiner

*Primary Examiner*—James O Wilson
*Assistant Examiner*—Ebenezer Sackey
(74) *Attorney, Agent, or Firm*—Sughrue Mion, PLLC

(57) ABSTRACT

Isoflavone compounds are described and recommended as therapeutic agents. Exemplified and preferred compounds are (a). Indications show compounds have good competitive binding to estrogen receptors. This is exemplified

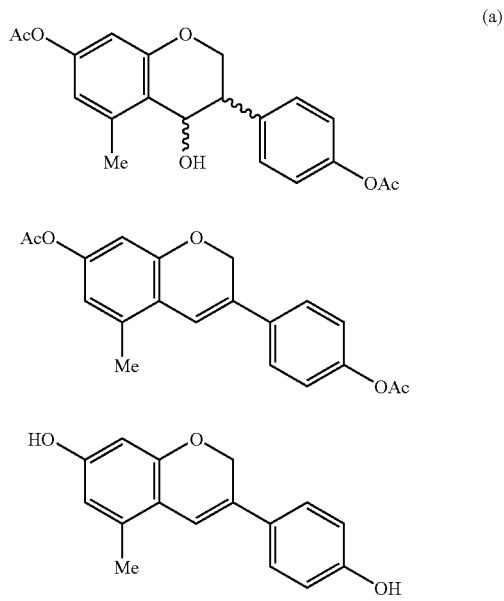

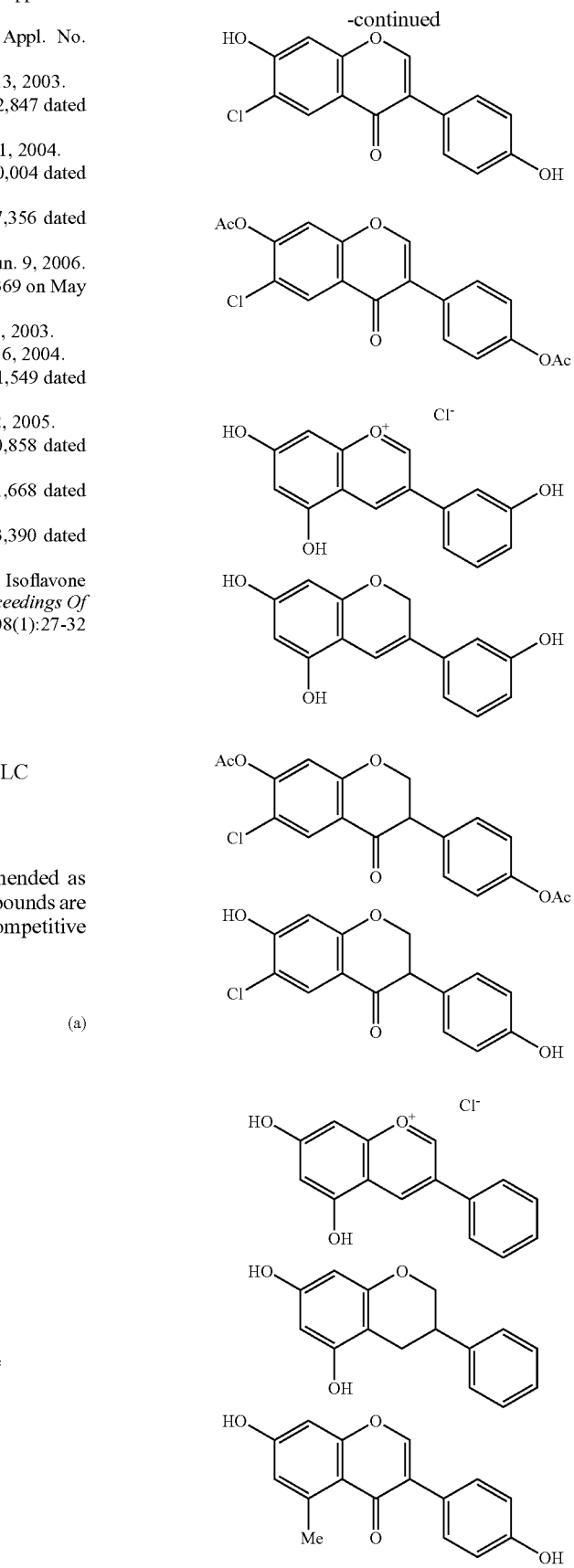

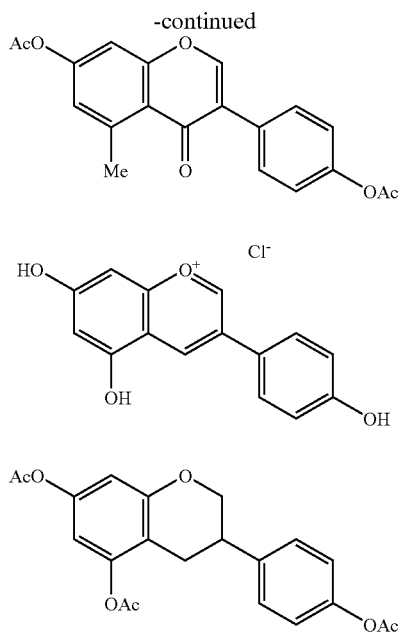
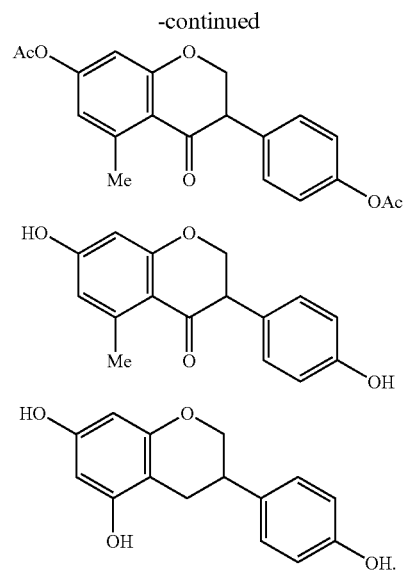
5 Claims, No Drawings

COMPOSITIONS AND THERAPEUTIC METHODS INVOLVING ISOFLAVONES AND ANALOGUES THEREOF

This application is a continuation application of U.S. application Ser. No. 10/070,361, which was accepted as a filing under 35 U.S.C. 371 on Jul. 8, 2002, now abandoned and which is a 371 filing of International Application No. PCT/AU00/01056, filed Sep. 6, 2000, and claims the benefit of Australian Application No. PQ-2661,filed Sep. 6, 1999, under 35 USC §§ 119 and 120. U.S. application Ser. No. 10/070,361; International Application No. PCT/AU00/01056; and Australian Application No. PQ-2661 are all incorporated by reference herein for any purpose.

This invention relates to compounds, formulations, drinks, foodstuffs, methods and therapeutic uses involving, containing, comprising, including and/or for preparing certain isoflavone compounds and analogues thereof.

According to an aspect of this invention there is provided isoflavone compounds and analogues thereof of the general formula I:

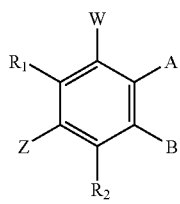

in which $R_1$ and $R_2$ are independently hydrogen, hydroxy, $OR_9$, $OC(O)R_{10}$, $OS(O)R_{10}$, CHO, $C(O)R_{10}$, COOH, $CO_2R_{10}$, $CONR_3R_4$, alkyl, haloalkyl, aryl, arylalkyl, thio, alkylthio, amino, alkylamino, dialkylamino, nitro or halo, Z is hydrogen, and W is $R_1$, A is hydrogen, hydroxy, $NR_3R_4$ or thio, and B is selected from

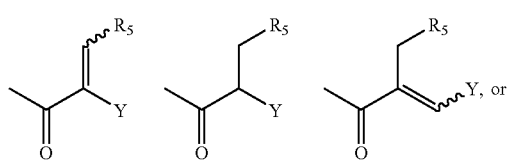

W is $R_1$, and A and B taken together with the carbon atoms to which they are attached form a six-membered ring selected from

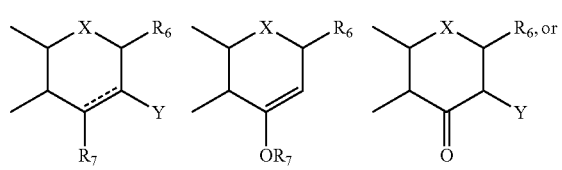

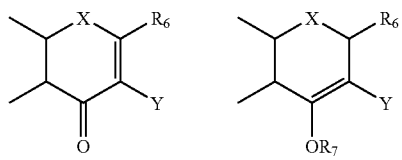

or

W, A and B taken together with the groups to which they are associated comprise

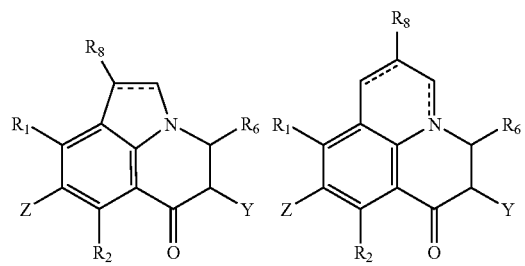

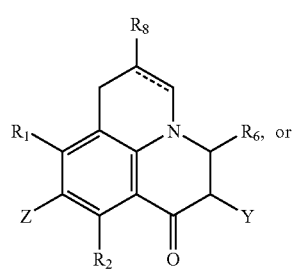

or

W, and A taken together with the groups to which they are associated comprise

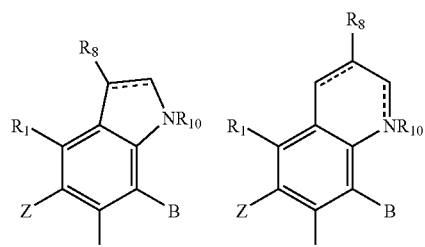

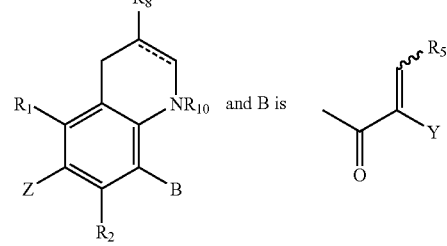 and B is 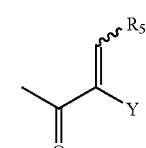

-continued

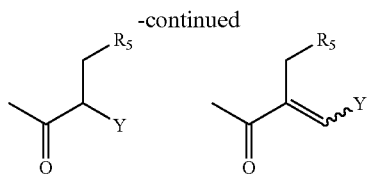

wherein
R$_3$ is hydrogen, alkyl, aryl, arylalkyl, an amino acid, C(O)R$_{11}$ where R$_{11}$ is hydrogen alkyl, aryl, arylalkyl or an amino acid, or CO$_2$R$_{12}$ where R$_{12}$ is hydrogen, alkyl, haloalkyl, aryl or arylalkyl,
R$_4$ is hydrogen, alkyl or aryl,
or R$_3$ and R$_4$ taken together with the nitrogen to which they are attached comprise pyrrolidinyl or piperidinyl,
R$_5$ is hydrogen, C(O)R$_{11}$ where R$_{11}$ is as previously defined, or CO$_2$R$_{12}$ where R$_{12}$ is as previously defined,
R$_6$ is hydrogen, hydroxy, alkyl, aryl, amino, thio, NR$_3$R$_4$, COR$_{11}$ where R$_{11}$ is as previously defined, CO$_2$R$_{12}$ where R$_{12}$ is as previously defined or CONR$_3$R$_4$,
R$_7$ is hydrogen, C(O)R$_{11}$ where R$_{11}$ is as previously defined, alkyl, haloalkyl, aryl, arylalkyl or Si(R$_{13}$)$_3$ where each R$_{13}$ is independently hydrogen, alkyl or aryl,
R$_8$ is hydrogen, hydroxy, alkoxy or alkyl,
R$_9$ is alkyl, haloalkyl, aryl, arylalkyl, C(O)R$_{11}$ where R$_{11}$ is as previously defined, or Si(R$_{13}$)$_3$ where R$_{13}$ is as previously defined,
R$_{10}$ is hydrogen, alkyl, haloalkyl, amino, aryl, arylalkyl, an amino acid, alkylamino or dialkylamino,
the drawing "- - - -" represents either a single bond or a double bond,
X is O, NR$_4$ or S, and
Y is

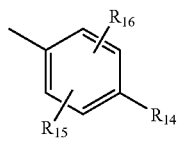

wherein
R$_{14}$, R$_{15}$ and R$_{16}$ are independently hydrogen, hydroxy, OR$_9$, OC(O)R$_{10}$, OS(O)R$_{10}$, CHO, C(O)R$_{10}$, COOH, CO$_2$R$_{10}$, CONR$_3$R$_4$, alkyl, haloalkyl, aryl, arylalkyl, thio, alkylthio, amino, alkylamino, dialkylamino, nitro or halo,
with the proviso that
when
R$_1$ is hydroxy, or OC(O)R$_A$ where R$_A$ is alkyl or an amino acid, and
R$_2$ is hydrogen, hydroxy, OR$_B$ where R$_B$ is an amino acid or C(O)R$_A$ where R$_A$ is as previously defined, and
W is hydrogen, then
Y is not 4-hydroxyphenyl or 4-alkylphenyl;
when
R$_1$ is hydroxy, or OC(O)R$_A$ where R$_A$ is alkyl or an amino acid, and
R$_2$ is hydrogen, hydroxy, OR$_B$ where R$_B$ is an amino acid or C(O)R$_A$ where R$_A$ is as previously defined, and
Y is 4-hydroxyphenyl or 4-alkylphenyl, then
W is not hydrogen;
when
R$_1$ is hydroxy, or OC(O)R$_A$ where R$_A$ is alkyl or an amino acid, and
Y is 4-hydroxyphenyl or 4-alkylphenyl, and
W is hydrogen, then
R$_2$ is not hydrogen, hydroxy, OR$_B$ where R$_B$ is an amino acid or C(O)R$_A$ where R$_A$ is as previously defined; and
when
R$_2$ is hydrogen, hydroxy, OR$_B$ where R$_B$ is an amino acid or C(O)R$_A$ where R$_A$ is as previously defined, and
Y is 4-hydroxyphenyl or 4-alkylphenyl, and
W is hydrogen, then
R$_1$ is not hydroxy, or OC(O)R$_A$ where R$_A$ is alkyl or an amino acid.

According to another aspect of this invention there is provided isoflavone compounds and analogues thereof of the general formula II:

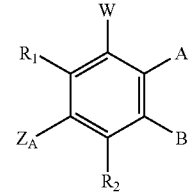

(II)

in which
R$_1$ and R$_2$ are independently hydrogen, hydroxy, OR$_9$, OC(O)R$_{10}$, OS(O)R$_{10}$, CHO, C(O)R$_{10}$, COOH, CO$_2$R$_{10}$, CONR$_3$R$_4$, alkyl, haloalkyl, aryl, arylalkyl, thio, alkylthio, amino, alkylamino, dialkylamino, nitro or halo,
Z$_A$ is OR$_9$, OC(O)R$_{10}$, OS(O)R$_{10}$, CHO, C(O)R$_{10}$, COOH, CO$_2$R$_{10}$, CONR$_3$R$_4$, alkyl, haloalkyl, aryl, arylalkyl, thio, alkylthio, amino, alkylamino, dialkylamino, nitro or halo, and
W is R$_1$, A is hydrogen, hydroxy, NR$_3$R$_4$ or thio, and B is selected from

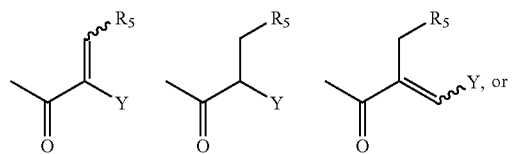

or
W is R$_1$, and A and B taken together with the carbon atoms to which they are attached form a six-membered ring selected from

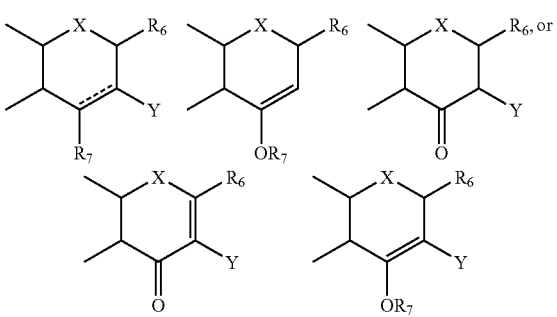

or

W, A and B taken together with the groups to which they are associated comprise

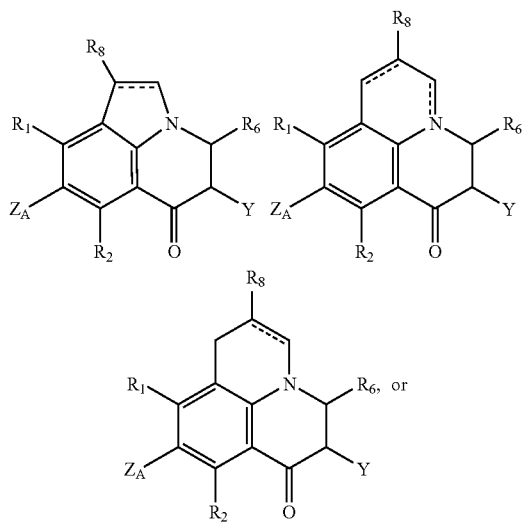

or

W and A taken together with the groups to which they are associated comprise

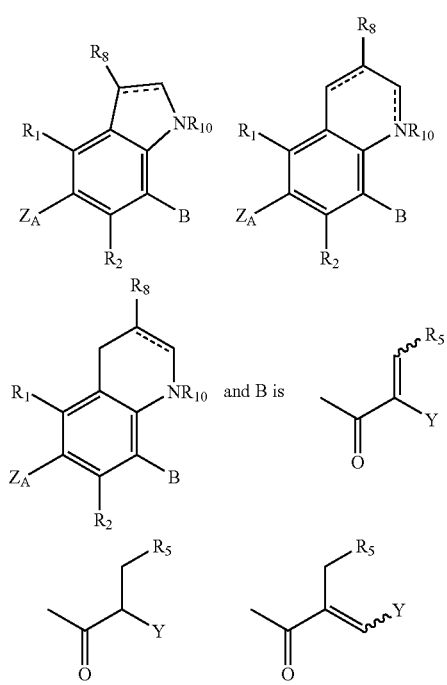

wherein $R_3$ is hydrogen, alkyl, aryl, arylalkyl, an amino acid, $C(O)R_{11}$ where $R_{11}$, is hydrogen alkyl, aryl, arylalkyl or an amino acid, or $CO_2R_{12}$ where $R_{12}$ is hydrogen, alkyl, haloalkyl, aryl or arylalkyl, $R_4$ is hydrogen, alkyl or aryl, or $R_3$ and $R_4$ taken together with the nitrogen which they are attached are pyrrolidinyl or piperidinyl, $R_5$ is hydrogen, $C(O)R_{11}$ where $R_{11}$ is as previously defined, or $CO_2R_{12}$ where $R_{12}$ is as previously defined, $R_6$ is hydrogen, hydroxy, alkyl, aryl, amino, thio, $NR_3R_4$, $COR_{11}$ where $R_{11}$ is as previously defined, $CO_2R_{12}$ where $R_{12}$ is as previously defined or $CONR_3R_4$, $R_7$ is hydrogen, $C(O)R_{11}$ where $R_{11}$ is as previously defined, alkyl, haloalkyl, aryl, arylalkyl or $Si(R_{13})_3$ where each $R_{13}$ is independently hydrogen, alkyl or aryl, $R_8$ is hydrogen, hydroxy, alkoxy or alkyl, $R_9$ is alkyl, haloalkyl, aryl, arylalkyl, $C(O)R_{11}$ where $R_{11}$ is as previously defined, or $Si(R_{13})_3$ where $R_{13}$ is as previously defined, $R_{10}$ is hydrogen, alkyl, haloalkyl, amino, aryl, arylalkyl, an amino acid, alkylamino or dialkylamino, the drawing "----" represents either a single bond or a double bond, X is O, $NR_4$ or S, and Y is

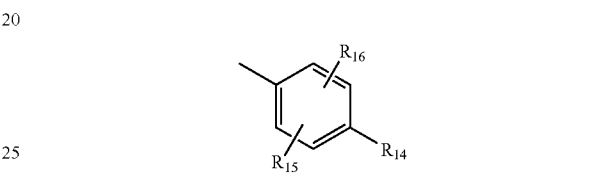

wherein $R_{14}$, $R_{15}$ and $R_{16}$ are independently hydrogen, hydroxy, $OR_9$, $OC(O)R_{10}$, $OS(O)R_{10}$, CHO, $C(O)R_{10}$, COOH, $CO_2R_{10}$, $CONR_3R_4$, alkyl, haloalkyl, aryl, arylalkyl, thio, alkylthio, amino, alkylamino, dialkylamino, nitro or halo.

It has surprisingly been found by the inventors that compounds of the general formulae I and II:

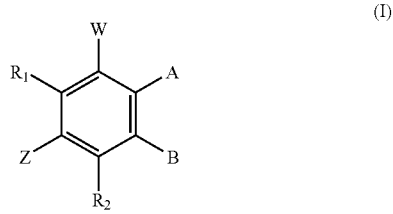

(I)

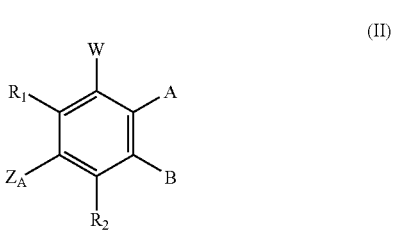

(II)

in which $R_1$, $R_2$, W, A, B, Z and $Z_A$ are as defined above have particular utility and effectiveness in the treatment, prophylaxis, amelioration defence against, and/or prevention of menopausal syndrome including hot flushes, anxiety, depression, mood swings, night sweats, headaches, and urinary incontinence; osteoporosis; premenstrual syndrome, including fluid retention, cyclical mastalgia, and dysmenorrhoea; Reynaud's Syndrome; Reynaud's Phenomenon; Buergers Disease; coronary artery spasm; migraine headaches; hypertension; benign prostatic hypertrophy; all forms of cancer including breast cancer; uterine cancer; ovarian cancer; testicular cancer; large bowel cancer; endometrial cancer; prostatic cancer; uterine cancer; atherosclerosis; Alzheimers disease; inflammatory diseases including inflammatory bowel disease, ulcerative colitis, Crohns disease; rheumatic diseases including rheumatoid arthritis; acne; baldness including male pattern baldness (alopecia hereditaria); psoriasis; diseases associated with oxidant stress including cancer; myocardial infarction; stroke; arthritis; sunlight induced skin damage or cataracts.

Thus according to another aspect of the present invention there is provided a method for the treatment, prophylaxis, amelioration, defence against, and/or prevention of menopausal syndrome including hot flushes, anxiety, depression, mood swings, night sweats, headaches, and urinary incontinence; osteoporosis; premenstrual syndrome, including fluid retention, cyclical mastalgia, and dysmenorrhoea; Reynaud's Syndrome; Reynaud's Phenomenon; Buergers Disease; coronary artery spasm; migraine headaches; hypertension; benign prostatic hypertrophy; all forms of cancer including breast cancer; uterine cancer; ovarian cancer; testicular cancer; large bowel cancer; endometrial cancer; prostatic cancer; uterine cancer; artherosclerosis; Alzheimers disease; inflammatory diseases including inflammatory bowel disease, ulcerative colitis, Crohns disease; rheumatic diseases including rheumatoid arthritis; acne; baldness including male pattern baldness (alopecia hereditaria); psoriasis; diseases associated with oxidant stress including cancer; myocardial infarction; stroke; arthritis; sunlight induced skin damage or cataracts (for convenience hereafter referred to as the "therapeutic indications") which comprises administering to a subject a therapeutically effective amount of one or more compounds of formulae I and II as defined above.

Yet another aspect of the present invention is the use of compounds of formulae I and II for the manufacture of a medicament for the treatment, amelioration, defence against, prophylaxis and/or prevention of one or more of the therapeutic indications.

Still another aspect of the present invention is the use of one or more compounds of formulae I and II in the treatment, amelioration, defence against, prophylaxis and/or prevention of one or more of the therapeutic indications.

And another aspect of the present invention comprises an agent for the treatment, prophylaxis, amelioration, defence against and/or treatment of the therapeutic indications which comprises one or more compounds of formulae I and II either alone or in association with one or more carriers or excipients.

A further aspect of the invention is a therapeutic composition which comprises one or more compounds of formulae I and II in association with one or more pharmaceutical carriers and/or excipients.

A still further aspect of the present invention is a drink or food-stuff, which contains one or more compounds of formulae I and II.

Another aspect of the present invention is a microbial culture or a food-stuff containing one or more microbial strains which microorganisms produce one or more compounds of formulae I and II.

Still another aspect of the present invention relates to one or more microorganisms which produce one or more compounds of formulae I and II. Preferably the microorganism is a purified culture, which may be admixed and/or administered with one or more other cultures which product compounds of formulae I and II.

Throughout this specification and the claims which follow, unless the text requires otherwise, the word "comprise", and variations such as "comprises" or "comprising", will be understood to imply the inclusion of a stated integer or step or group of integers or steps but not the exclusion of any other integer or step or group of integers or steps.

The term "alkyl" is taken to mean both straight chain and branched chain alkyl groups such as methyl, ethyl, propyl, isopropyl, butyl, isobutyl, secbutyl, tertiary butyl, and the like. The alkyl group has 1 to 10 carbon atoms, preferably from 1 to 6 carbon atoms, more preferably methyl, ethyl propyl or isopropyl. The alkyl group may optionally be substituted by one or more of fluorine, chlorine, bromine, iodine, carboxyl, $C_1$-$C_4$-alkoxycarbonyl, $C_1$-$C_4$-alkylamino-carbonyl, di-($C_1$-$C_4$-alkyl)-amino-carbonyl, hydroxyl, $C_1$-$C_4$-alkoxy, formyloxy, $C_1$-$C_4$-alkyl-carbonyloxy, $C_1$-$C_4$-alkylthio, $C_3$-$C_6$-cycloalkyl or phenyl.

The term "aryl" is taken to include phenyl and naphthyl and may be optionally substituted by one or more $C_1$-$C_4$-alkyl, hydroxy, $C_1$-$C_4$-alkoxy, carbonyl, $C_1$-$C_4$-alkoxycarbonyl, $C_1$-$C_4$-alkylcarbonyloxy or halo.

The term "halo" is taken to include fluoro, chloro, bromo and iodo, preferably fluoro and chloro, more preferably fluoro. Reference to for example "haloalkyl" will include monohalogenated, dihalogenated and up to perhalogenated alkyl groups. Preferred haloalkyl groups are trifluoromethyl and pentafluoroethyl.

Particularly preferred compounds of the present invention are selected from:

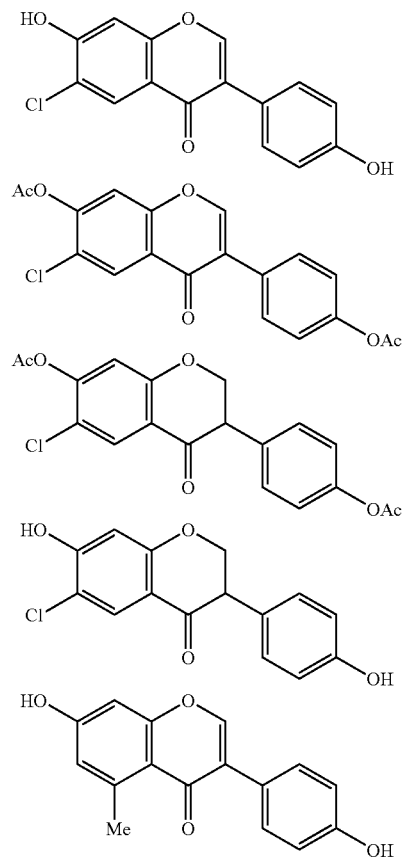

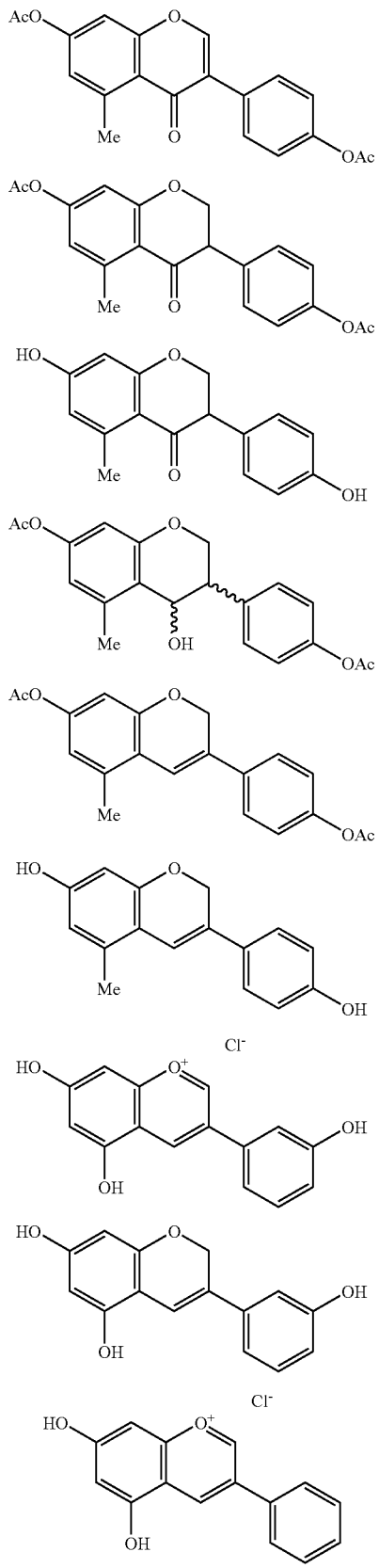

Compounds of the present invention have particular application in the treatment of diseases associated with or resulting from estrogenic effects, androgenic effects, vasodilatory and spasmodic effects, inflammatory effects and oxidative effects.

The amount of one or more compounds of formulae I and II which is required in a therapeutic treatment according to the invention will depend upon a number of factors, which include the specific application, the nature of the particular compound used, the condition being treated, the mode of administration and the condition of the patient. Compounds of formulae I or II may be administered in a manner and amount as is conventionally practised. See, for example, Goodman and Gilman, *The Pharmacological Basis of Therapeutics*, 1299 (7th Edition, 1985). The specific dosage utilised will depend upon the condition being treated, the state of the subject, the route of administration and other well known factors as indicated above. In general, a daily dose per patient may be in the range of 0.1 mg to 2 g; typically from 0.5 mg to 1 g; preferably from 50 mg to 200 mg.

The production of pharmaceutical compositions for the treatment of the therapeutic indications herein described are typically prepared by admixture of the compounds of the invention (for convenience hereafter referred to as the "active compounds", with one or more pharmaceutically or veterinarially acceptable carriers and/or excipients as are well known in the art.

The carrier must, of course, be acceptable in the sense of being compatible with any other ingredients in the formulation and must not be deleterious to the subject. The carrier or excipient may be a solid or a liquid, or both, and is preferably formulated with the compound as a unit-dose, for example, a tablet, which may contain from 0.5% to 59% by weight of the active compound, or up to 100% by weight of the active compound. One or more active compounds may be incorporated in the formulations of the invention, which may be prepared by any of the well known techniques of pharmacy consisting essentially of admixing the components, optionally including one or more accessory ingredients.

The formulations of the invention include those suitable for oral, rectal, optical, buccal (for example, sublingual), parenteral (for example, subcutaneous, intramuscular, intradermal, or intravenous) and transdermal administration, although the most suitable route in any given case will depend on the nature and severity of the condition being treated and on the nature of the particular active compound which is being used.

Formulation suitable for oral administration may be presented in discrete units, such as capsules, sachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture such as to form a unit dosage. For example, a tablet may be prepared by compressing or moulding a powder or granules containing the active compound, optionally with one or more accessory ingredients. Compressed tablets may be prepared by compressing, in a suitable machine, the compound of the free-flowing, such as a powder or granules optionally mixed with a binder, lubricant, inert diluent, and/or surface active/dispersing agent(s). Moulded tablets may be made by moulding, in a suitable machine, the powdered compound moistened with an inert liquid binder.

Formulations suitable for buccal (sublingual) administration include lozenges comprising the active compound in a flavoured base, usually sucrose and acacia or tragacanth; and pastilles comprising the compound in an inert base such as gelatin and glycerin or sucrose and acacia.

Compositions of the present invention suitable for parenteral administration conveniently comprise sterile aqueous preparations of the active compounds, which preparations are preferably isotonic with the blood of the intended recipient. These preparations are preferably administered intravenously, although administration may also be effected by means of subcutaneous, intramuscular, or intradermal injection. Such preparations may conveniently be prepared by admixing the compound with water or a glycine buffer and rendering the resulting solution sterile and isotonic with the blood. Injectable formulations according to the invention generally contain from 0.1% to 60% w/v of active compound and are administered at a rate of 0.1 ml/minute/kg.

Formulations suitable for rectal administration are preferably presented as unit dose suppositories. These may be prepared by admixing the active compound with one or more conventional solid carriers, for example, cocoa butter, and then shaping the resulting mixture.

Formulations or compositions suitable for topical administration to the skin preferably take the form of an ointment, cream, lotion, paste, gel, spray, aerosol, or oil. Carriers which may be used include Vaseline, lanoline, polyethylene glycols, alcohols, and combination of two or more thereof. The active compound is generally present at a concentration of from 0.1% to 0.5% w/w, for example, from 0.5% to 2% w/w. Examples of such compositions include cosmetic skin creams.

Formulations suitable for transdermal administration may be presented as discrete patches adapted to remain in intimate contact with the epidermis of the recipient for a prolonged period of time. Such patches suitably contain the active compound as an optionally buffered aqueous solution of, for example, 0.1 M to 0.2 M concentration with respect to the said active compound.

Formulations suitable for transdermal administration may also be delivered by iontophoresis (see, for example, *Pharmaceutical Research* 3 (6), 318 (1986)) and typically take the form of an optionally buffered aqueous solution of the active compound. Suitable formulations comprise citrate or bis/tris buffer (pH 6) or ethanol/water and contain from 0.1 M to 0.2 M active ingredient.

The active compounds may be provided in the form of food stuffs, such as being added to, admixed into, coated, combined or otherwise added to a food stuff. The term food stuff is used in its widest possible sense and includes liquid formulations such as drinks including dairy products and other foods, such as health bars, desserts, etc. Food formulations containing compounds of the invention can be readily prepared according to standard practices.

Compounds of the present invention have potent antioxidant activity and thus find wide application in pharmaceutical and veterinary uses, in cosmetics such as skin creams to prevent skin ageing, in sun screens, in foods, health drinks, shampoos, and the like.

It has surprisingly been found that compounds of the formulae I or II interact synergistically with vitamin E to protect lipids, proteins and other biological molecules from oxidation.

Accordingly a further aspect of this invention provides a composition comprising one or more compounds of formulae I or II, vitamin E, and optionally a pharmaceutically, veterinarially or cosmetically acceptable carriers and/or excipients.

Therapeutic methods, uses and compositions may be for administration to humans or animals, such as companion and domestic animals (such as dogs and cats), birds (such as chickens, turkeys, ducks), livestock animals (such as cattle, sheep, pigs and goats) and the like.

Compounds of formulae I and II may be prepared by standard methods known to those skilled in the art. Suitable methods may be found in, for example, International Patent Application WO 98/08503 which is incorporated herein in its entirety by reference. Methods which may be employed by those skilled in the art of chemical synthesis for constructing the general ring structures depicted in formulae I and II are depicted in schemes 1-8 below. Chemical functional group protection, deprotection, synthons and other techniques known to those skilled in the art may be used where appropriate in the synthesis of the compounds of the present invention. In the formulae depicted in the schemes below the moieties $R_1$, $R_2$, $R_6$, $R_8$, $R_{14}$, $R_{15}$, $R_{16}$, W and X are as defined above. The moiety T is either Z or $Z_A$ as defined in formulae I or II above. Reduction of the isoflavone derivatives may be effected by procedures well-known to those skilled in the art including sodium borohydride reduction, and hydration over metal catalysts such as Pd/C, Pd/CaCO$_3$ and Platinum(IV) oxide (Adam's catalyst) in protic or aprotic solvents. The end products and isomeric ratios can be varied depending on the catalyst/solvent system chosen. The schemes depicted below are not to be considered limiting on the scope of the invention described herein.

Scheme 1
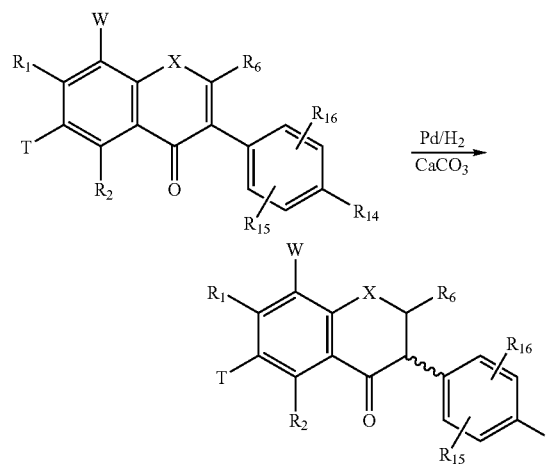
Scheme 2
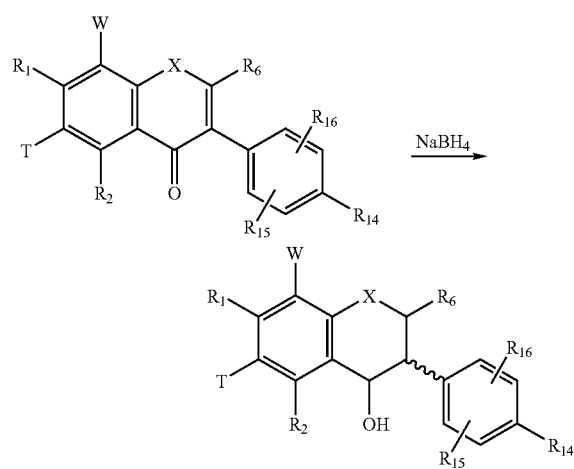
Scheme 3
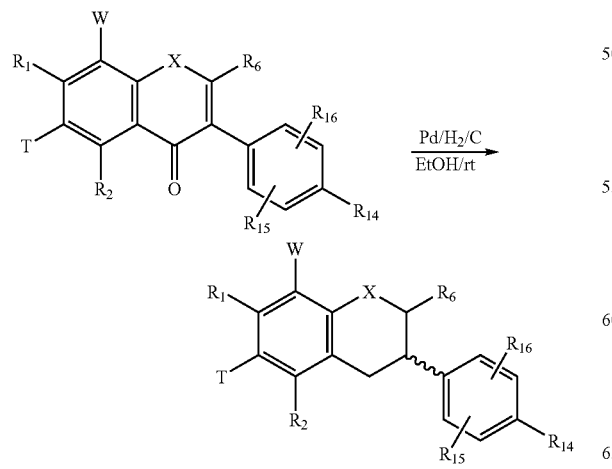
Scheme 4
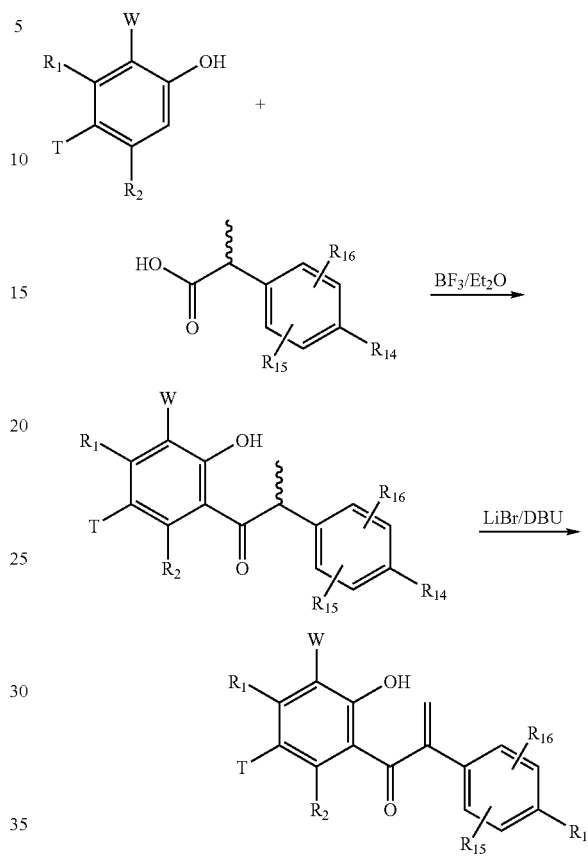
Scheme 5
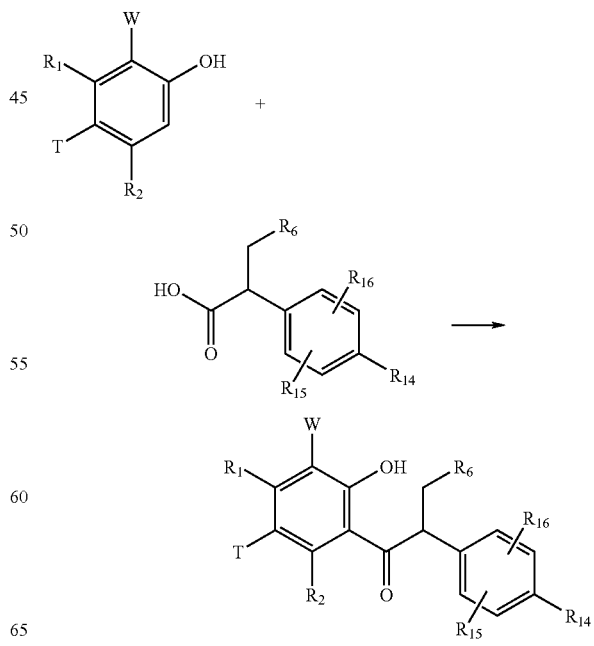

Scheme 6
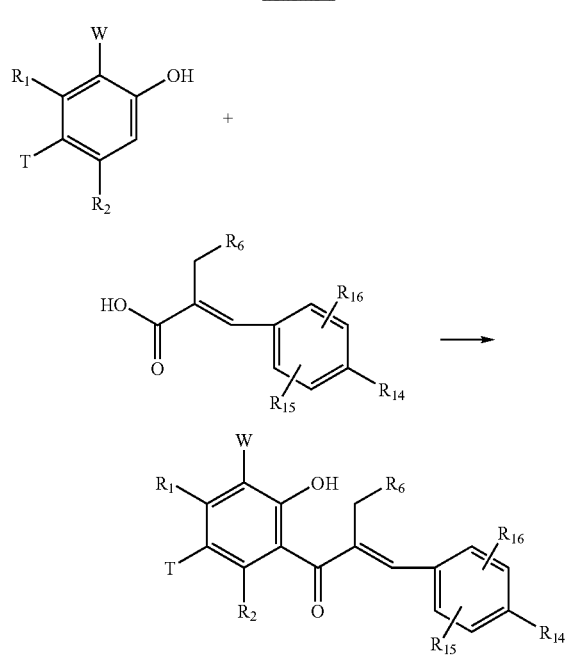
Scheme 7
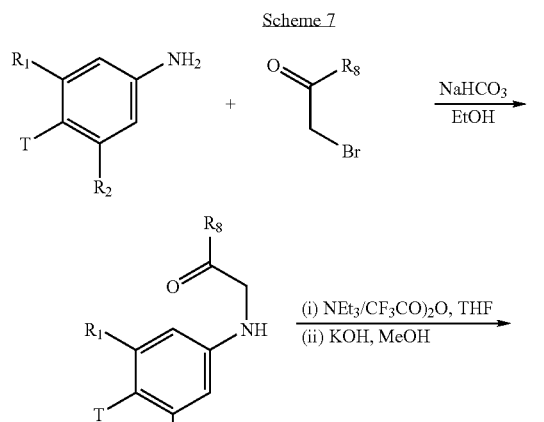
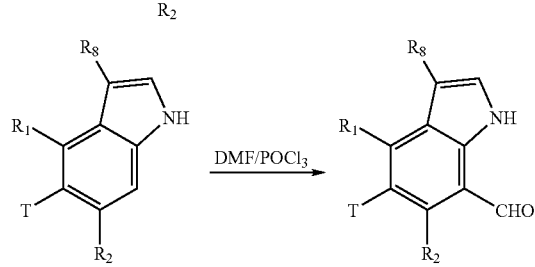
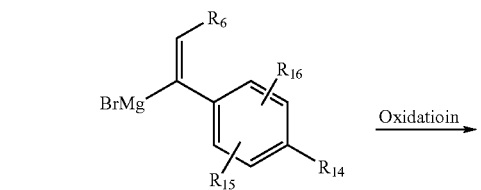
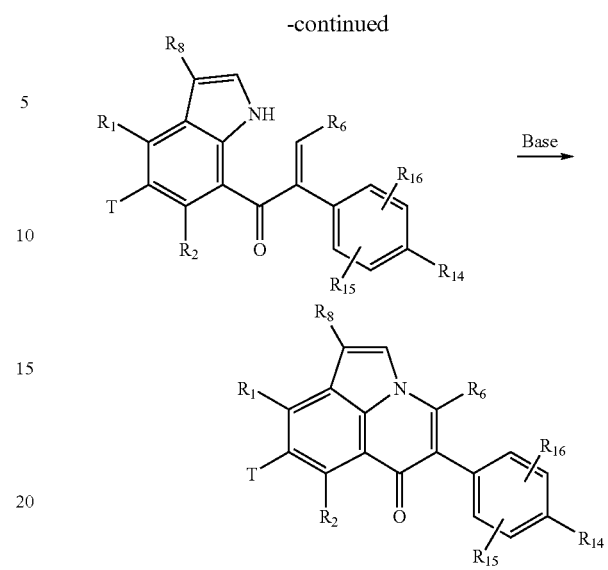
Scheme 8
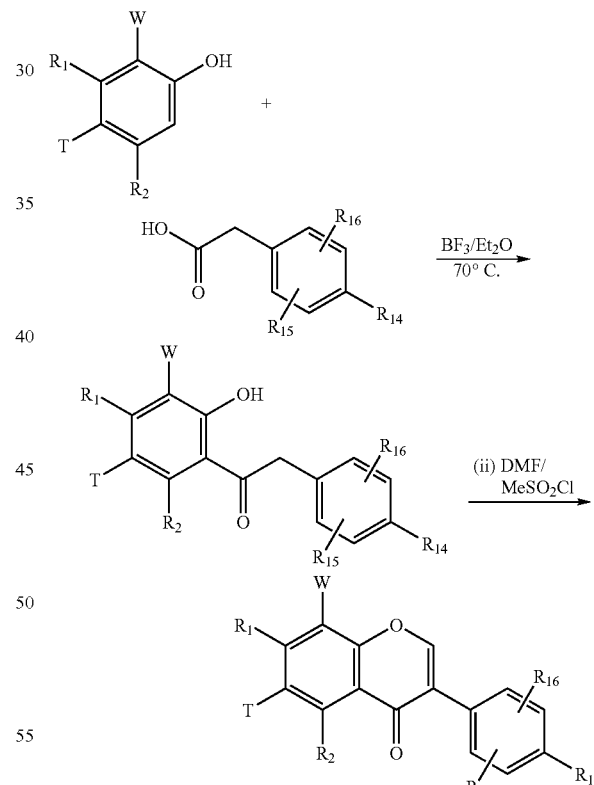
EXAMPLE 1
General Syntheses of Substituted Isoflavones
6-Chloro-4',7-dihydroxyisoflavone was synthesised by the condensation of 4-chlororesorcinol with 4-hydroxyphenylacetic acid to afford 5-chloro-2,4,4'-trihydroxydeoxybenzoin. Cyclisation of the intermediate deoxybenzoin was achieved by treatment with dimethylformamide and methanesulfonyl chloride in the presence of boron triflouride etherate.

By varying the substitution pattern on the resorcinol or phenylacetic acid groups numerous other substituted isoflavones can also be synthesised in a similar manner. For example starting with 5-methyl resorcinol affords 4',7-dihydroxy-5-methylisoflavone, whilst use of 3-hydroxy phenyl acetic acid in the general synthetic method affords 3'-hydroxy isoflavone derivatives.

Isoflavan-4-ones

EXAMPLE 2

Synthesis of 6-Chloro-4',7-diacetoxyisoflavone

A mixture of 6-chloro-4',7-dihydroxyisoflavone (1.25 g, 4.3 mmol), acetic anhydride (7.5 ml) and pyridine (1.4 ml) was heated in an oil bath at 105-110° C. for 1 h. After cooling the mixture to room temperature, it was stirred for a further 30 min during which time the diacetate crystallised from the solution. The product was filtered, washed thoroughly with aqueous methanol (50%) and dried to yield 6-chloro-4',7-diacetoxyisoflavone (1.2 g, 75%) as colourless prisms. $^1$H NMR (CDCl$_3$): δ 2.32 (s, 3H, OCOCH$_3$), 2.41 (s, 3H, OCOCH$_3$), 7.16 (d, 2H, J 8.6 Hz, ArH), 7.36 (s, 1H, H8), 7.57 (d, 2H, J 8.6 Hz, ArH), 8.00 (s, 1H, H5), 8.37 (s, 1H, H2).

EXAMPLE 3

Synthesis of 6-Chloro-4',7-Diacetoxyisoflavan4-one

Adam's catalyst (0.045 g) was added to a solution of 6-chloro-4',7-diacetoxyisoflavone (0.25 g, 0.7 mmol) in ethyl acetate (30 ml) and the mixture was stirred at room temperature under a hydrogen atmosphere for 24 h. The catalyst was removed by filtration through Celite and the resulting filtrate was evaporated in vacuo. The residue was recrystallised from ethanol to yield 6-chloro-4',7-diacetoxyisoflavan4-one (0.15 g, 60%) as colourless plates. $^1$H NMR (CDCl$_3$): δ 2.29 (s, 3H, OCOCH$_3$), 2.37 (s, 3H, OCOCH$_3$), 3.98 (dd, 1H, J 6.0 Hz, 7.5 Hz, H3), 4.68 (m, 2H, H2), 6.87 (s, 1H, H8), 7.07 (d, 2H, J 8.6 Hz, ArH), 7.27 (d, 2H, J 8.6 Hz, ArH), 8.01 (s, 1H, H5).

EXAMPLE 4

Synthesis of 6-Chloro-4',7-dihydroxyisoflavan4-one

Imidazole (0.60 g) was added to a suspension of 6-chloro-4',7-diacetoxyisoflavan-4-one (0.24 g, 0.06 mmol) in absolute ethanol (5.0 ml) and the mixture was refluxed for 45 min under argon. The solution was concentrated under reduced pressure and distilled water (10 ml) was added to the residue. The mixture was left overnight in the fridge and the resulting precipitate was filtered, washed with water and dried to yield 6-chloro-4',7-dihydroxyisoflavan-4-one (0.14 g, 75%) as a white powder. 1H NMR (d$_6$-acetone): δ 3.87 (t, 1H, J 7.2 Hz, H3), 4.64 (d, 2H, J 6.2 Hz, H2), 6.59 (s, 1H, H8), 6.78 (d, 2H, J 8.7 Hz, ArH), 7.10 (d, 2H, J 8.7 Hz, ArH), 7.70 (bs, 1H, OH), 7.77 (s, 1H, H5).

EXAMPLE 5

Synthesis of 4',7-Diacetoxy-5-methylisoflavone

A mixture of 4',7-dihydroxy-5-methylisoflavone (1.51 g, 5.6 mmol), acetic anhydride (9 ml) and pyridine (1.7 ml) was heated in an oil bath at 105-110° C. for 1 h. After cooling the mixture to room temperature, it was stirred for a further 30 min during which time the diacetate crystallised from the solution. The product was filtered, washed thoroughly with water and recrystallised from methanol to yield 4',7-diacetoxy-5-methylisoflavone as colourless prisms (1.8 g, 91%). m.p. 195-97° C., $^1$H NMR (CDCl$_3$): δ 2.32 (s, 3H, OCOCH$_3$), 2.35 (s, 3H, OCOCH$_3$), 2.87 (s, 3H, Me), 6.92 (bs, 1H, H8), 7.12 (bs, 1H, H5), 7.16 (d, 2H, J 8.7 Hz, ArH), 7.55 (d, 2H, J 8.7 Hz, ArH), 7.89 (s, 1H, H2).

EXAMPLE 6

Synthesis of 4',7-Diacetoxy-5-methylisoflavan4-one

Palladium on barium sulfate (5%, 0.06 g) was added to a solution of 4',7-diacetoxy-5-methylisoflavone (0.30 g, 0.8 mmol) in ethyl acetate (50 ml) and the mixture was stirred at room temperature under a hydrogen atmosphere for 24 h. The catalyst was removed by filtration through Celite and the resulting filtrate was evaporated in vacuo. The residue was recrystallised from ethanol to yield 4',7-diacetoxy-5-methylisoflavan-4-one (0.20 g, 67%) as colourless plates. m.p. 143-45° C., $^1$H NMR (CDCl$_3$): δ 2.29 (s, 3H, OCOCH$_3$), 2.30 (s, 3H, OCOCH$_3$), 2.62 (s, 3H, Me), 3.95 (t, 1H, J 7.2 Hz, H3), 4.62 (d, 2H, J 6.8 Hz, H2), 6.59 (d, 1H, J 2.2 Hz, H8), 6.66 (d, 1H, J 2.2 Hz, H5), 7.07 (d, 2H, J 8.3 Hz, ArH), 7.28 (d, 2H, J 8.3 Hz, ArH).

EXAMPLE 7

Synthesis of 4',7-Dihydroxy-5-methylisoflavanone

Imidazole (0.63 g) was added to a suspension of 4',7-diacetoxy-5-methylisoflavan-4-one (0.50 g, 1.4 mmol) in absolute ethanol (20.0 ml) and the mixture was refluxed for 45 min under argon. The solution was concentrated under reduced pressure and distilled water (10 ml) was added to the residue. The mixture was left overnight in the fridge and the resulting precipitate was filtered, washed with water and dried to yield 4',7-dihydroxy-5-methylisoflavan-4-one (0.25 g, 66%) as a white powder. $^1$H NMR (d$_6$-acetone): δ 2.51 (s, 3H, Me), 3.76 (t, 1H, J 5.7 Hz, H3), 4.57 (d, 2H, J 7.1 Hz, H2), 6.26 (d, 1H, J 2.2 Hz, H8), 6.35 (d, 1H, J 2.2 Hz, H5), 6.78 (d, 2H, J 8.7 Hz, ArH), 7.11 (d, 2H, J 8.7 Hz, ArH).

Isolflavan-4-ols and Isoflav-3-enes

EXAMPLE 8

Synthesis of 4'-7-Diacetoxy-5-methylisoflavan-4-ol

4'-7-Diacetoxy-5-methylisoflavan-4-ol was prepared by the reduction of 4'-7-diacetoxy-5-methylisoflavone (0.25 g) with Adam's catalyst in ethyl acetate (30 ml) under a hydrogen atmosphere for 72 hours. The solution was filtered through a pad of Celite to yield predominantly cis4'-7-diacetoxy-5-methylisoflavan-4-ol. $^1$H NMR (CDCl$_3$): δ 2.26 (s, 3H, OCOCH$_3$), 2.30 (s, 3H, OCOCH$_3$), 2.62 (s, 3H, Me), 3.24 (dt, 1H, J 3.4 Hz, J 11.8 Hz, H3), 4.31 (ddd, 1H, J 1.4 Hz, 3.6 Hz, 10.5 Hz, H2); 4.57 (dd, 1H, J 10.5 Hz, 11.8 Hz, H2), 4.82

(bs, 1H, H4), 6.51 (d, 1H, J 2.1 Hz, H8), 6.59 (d, 1H, J 2.1 Hz, H6), 7.06 (d, 2H, J 8.6 Hz, ArH), 7.29 (d, 2H, J 8.6 Hz ArH).

EXAMPLE 9

Synthesis of 4',7-Diacetoxy-5-methylisoflav-3-ene

4',7-Diacetoxy-5-methylisoflav-3-ene was prepared by the dehydration of cis- and trans-4'-7-diacetoxy-5-methylisoflavan-4-ol (0.2 g) with phosphorus pentoxide (2.0 g) in dry dichloromethane (20 ml). The crude product was chromatographed on silica column using dichloromethane as the eluent. $^1$H NMR (CDCl$_3$): δ 2.28 (s, 3H, OCOCH$_3$), 2.31 (s, 3H, OCOCH$_3$), 2.36 (s, 3H, Me), 5.08 (s, 2H, H2), 6.49 (d, 1H, J 2.0 Hz, H8), 6.52 (d, 1H, J 2.2 Hz, H5), 6.89 (s, 1H, H4), 7.14 (d, 2H, J 8.6 Hz, ArH), 7.44 (d, 2H, J 8.6 Hz, ArH).

EXAMPLE 10

Synthesis of 4',7-Dihydroxy-5-methylisoflav-3-ene

4',7-Dihydroxy-5-methylisoflav-3-ene was prepared from 4',7-diacetoxy-5-methylisoflav-3-ene by the removal of the acetoxy groups by hydrolysis under standard conditions.

EXAMPLE 11

Synthesis of 3',5,7-Trihydroxyisoflavylium chloride

Phosphoryl chloride (1.75 ml) was added to a mixture of the monoaldehyde (0,95 g) and phloroglucinol dihydrate (1.6 g) in acetonitrile (10 ml). The mixture was stirred at 30° C. for 20 minutes and then at room temperature for 3 hours. The orange precipitate was filtered and washed with acetic acid to yield the isoflavylium salt.

EXAMPLE 12

Synthesis of Isoflav-3-ene-3',5,7-triol

Isoflav-3-ene-3',5,7-triol was prepared by the reduction of 3',5,7-trihydroxyisoflavylium chloride (0.5 g) with sodium cyanoborohydride (0.33 g) in ethyl acetate (11 ml) and acetic acid (3 ml) and chromatographic separation of the resulting mixture of isoflav-3-ene and isoflav-2-ene mixture. $^1$H NMR (d$_6$-acetone): 67 4.99 (s, 2H, H2), 5.92 (d, 1H, J 2.0 Hz, ArH), 6.04 (d, 1H, J 2.2 Hz, ArH), 6.78-7.18 (m, 5H, ArH).

Isoflavans

EXAMPLE 13

Synthesis of Isoflavan-5,7-diol

Isoflavan-5,7-diol was prepared by the reduction of a suspension of 5,7-dihydroxyisoflavylium chloride (0.5 g) with Palladium-on-charcoal (5%, 0.1 g) in acetic acid (15 ml) containing ethyl acetate (2.5 ml) under a hydrogen atmosphere. The crude product was recrystallised from 1,2-dichloromethane to give the isoflavan as colourless needles, m.p. 76-78° C. (lit m.p. 77-79° C.).

EXAMPLE 14

Synthesis of 4',5,7-Triacetoxyisoflavan

4',5,7-Triacetoxyisoflavan was prepared by the reduction of a suspension of 4', 5,7-trihydroxyisoflavylium chloride (0.31 g) with platinum oxide (0.04 g) in a mixture of acetic anhydride (2.0 ml) and ethyl acetate (10 ml) under a hydrogen atmosphere. After the removal of catalyst the crude product was refluxed with pyridine (0.5 ml) and the resulting triacetate was isolated by evaporation of the solvent and crystallisation of the residue. M.p. 126-28° C.

EXAMPLE 15

Synthesis of Isoflavan-4',5,7-triol

Isoflavan-4',5,7-triol was prepared from 4',5,7-triacetoxyisoflavan by the removal of the acetyl groups by hydrolysis. M.p. 206-8° C.

EXAMPLE 16

The binding affinity of various compounds of the invention for both subtypes of the estrogen receptor was determined with the "Estrogen Receptor Alpha or Beta Competitor Assay Core HTS Kit" supplied by Panvera Corporation (Product No. P2614/2615). 6-Chloro-4',7-dihydroxyisoflavan-4-one showed good competitive binding to the estrogen receptor with the following results:

ER alpha receptor=37.82 uM
ER beta receptor=32.14 uM

The results show that the compounds of the present invention have particular application in the treatment of diseases associated with or resulting from estrogenic effects, androgenic effects, vasodilatory and spasmodic effects, inflammatory effects and oxidative effects.

Those skilled in the art will appreciate that the invention described herein is susceptible to variations and modifications other than those specifically described. It is to be understood that the invention includes all such variations and modifications. The inventions also includes all of the steps, features, compositions and compounds referred to or indicated in the specification, individually or collectively, and any and all combinations of any two or more of said steps or features.

The claims defining the invention are as follows:
1. A compound of formula:

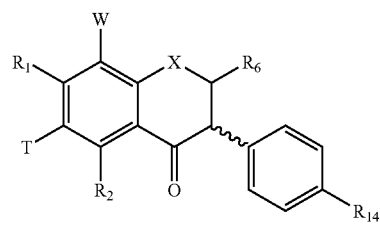

wherein: $R_1$ and $R_2$ are independently chosen from hydrogen, hydroxy, OC(O)$R_{10}$ and alkyl,
W is chosen from hydrogen, halo, and alkyl,
X is O,
T is chosen from hydrogen, halo, and alkyl,
$R_6$ is hydrogen,
$R_{14}$ is independently chosen from hydroxy, OR$_9$, OC(O)R$_{10}$, OS(O)R$_{10}$, CHO, C(O)R$_{10}$, COOH, CO$_2$R$_{10}$, CONR$_3$R$_4$, alkyl, haloalkyl, aryl, arylalkyl, thio, alkylthio, amino, alkylamino, dialkylamino, nitro, and halo,
$R_3$ is chosen from hydrogen, alkyl, aryl, arylalkyl, an amino acid, C(O)R$_{11}$ where R$_{11}$ is hydrogen alkyl, aryl, arylalkyl, an amino acid, and CO$_2$R$_{12}$ where R$_{12}$ is hydrogen, alkyl, aryl, or arylalkyl;

R$_4$ is chosen from hydrogen, alkyl, and aryl;

or R$_3$ and R$_4$ taken together with the nitrogen to which they are attached are chosen from pyrrolidinyl and piperidinyl;

R$_9$ is chosen from alkyl, haloalkyl, aryl, arylalkyl, C(O)R$_{11}$, and Si(R$_{13}$)$_3$ where each R$_{13}$ is independently chosen from hydrogen, alkyl, and aryl; and R$_{10}$ is chosen from hydrogen, alkyl, haloalkyl, amino, aryl, arylalkyl, an amino acid, alkylamino, and dialkylamino;

with the proviso that when R$_1$ is hydrogen, hydroxy or OC(O)R$_A$ is alkyl or an amino acid, R$_2$ is hydrogen, hydroxy, or OC(O)R$_A$ where R$_A$ is as previously defined, T is hydrogen, and W is hydrogen, then R$_{14}$ is not hydroxy, acyloxy, methoxy, or alkyl.

2. A compound according to claim 1 wherein halo is selected from chloro and bromo.

3. A compound according to claim 1 selected from:

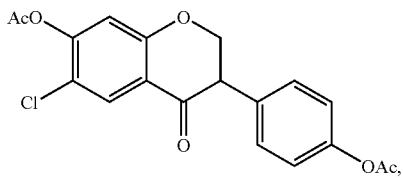

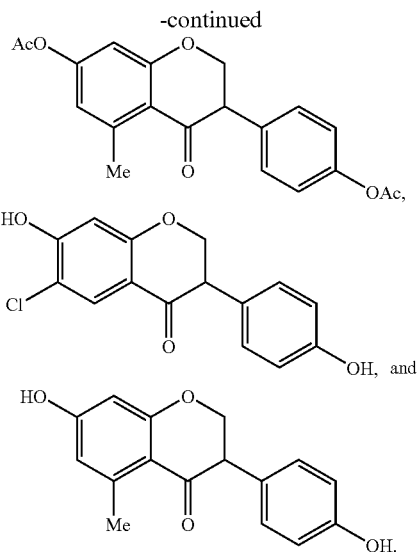

4. A composition comprising one or more compounds as defined in claim 1 with one or more pharmaceutical carriers and/or excipients.

5. A drink or food-stuff comprising one or more compounds as defined in claim 1.

* * * * *